(12) United States Patent
Greene et al.

(10) Patent No.: US 9,133,270 B2
(45) Date of Patent: Sep. 15, 2015

(54) ANTIBODY-LIKE PROTEINS FOR THERAPEUTIC AND DIAGNOSTIC USE

(75) Inventors: Mark I. Greene, Penn Valley, PA (US); Hongtao Zhang, Paoli, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 81 days.

(21) Appl. No.: 14/003,989

(22) PCT Filed: Mar. 8, 2012

(86) PCT No.: PCT/US2012/028286
§ 371 (c)(1),
(2), (4) Date: Dec. 17, 2013

(87) PCT Pub. No.: WO2012/122378
PCT Pub. Date: Sep. 13, 2012

(65) Prior Publication Data
US 2014/0178375 A1    Jun. 26, 2014

Related U.S. Application Data

(60) Provisional application No. 61/450,435, filed on Mar. 8, 2011.

(51) Int. Cl.
| | | |
|---|---|---|
| *C07K 16/18* | (2006.01) | |
| *C07K 16/32* | (2006.01) | |
| *C07K 7/06* | (2006.01) | |
| *A61K 39/00* | (2006.01) | |

(52) U.S. Cl.
CPC . *C07K 16/18* (2013.01); *C07K 7/06* (2013.01); *C07K 16/32* (2013.01); *A61K 2039/505* (2013.01); *C07K 2317/524* (2013.01); *C07K 2317/72* (2013.01); *C07K 2317/73* (2013.01); *C07K 2317/92* (2013.01); *C07K 2319/00* (2013.01); *C07K 2319/21* (2013.01); *C07K 2319/30* (2013.01)

(58) Field of Classification Search
CPC .... C07K 2310/30; C07K 16/18; C07K 16/32; C07K 2318/00–2318/20
See application file for complete search history.

(56) References Cited

U.S. PATENT DOCUMENTS

| | | | |
|---|---|---|---|
| 6,949,245 B1 | 9/2005 | Sliwkowski | |
| 7,638,598 B2 * | 12/2009 | Greene et al. | 530/300 |
| 7,662,374 B2 | 2/2010 | Greene et al. | |
| 8,728,479 B2 * | 5/2014 | Greene et al. | 424/178.1 |
| 8,962,793 B2 * | 2/2015 | Greene et al. | 530/300 |
| 2005/0202534 A1 * | 9/2005 | Ledbetter et al. | 435/69.1 |
| 2006/0134105 A1 * | 6/2006 | Lazar et al. | 424/133.1 |

FOREIGN PATENT DOCUMENTS

| | | |
|---|---|---|
| CN | 1370082 A | 9/2002 |
| WO | WO 01/00245 A2 | 1/2001 |
| WO | WO 02/081649 A2 | 10/2002 |
| WO | WO 2012/122378 A3 | 11/2013 |

OTHER PUBLICATIONS

Altschul, et al, "Methods for Assessing The Statistical Significance of Molecular Sequence Features by Using General Scoring Schemes", Mar. 1990, Proc. Natl. Acad. Sci. USA, 87:2264-2268.

Cho et al., "Structure of the Extracellular Region of Her2 Alone and in Complex With the Herceptin Fab", Nature, Feb. 13, 2003, 421(6924),756-760.

Diaz-Araya, et al, "Immunohistochemical and Topographic Studies of Dendritic Cells and Macrophages in Human Fetal Cornea", Investigative Ophthalmology & Visual Science, Mar. 1995, 36(3), 644-656.

Drebin, J.A., et al., "Monoclonal Antibodies Identify a Cell-Surface Antigen Associated with an Activated Cellular Oncogene", Nature, Dec. 1984, 312, 545-548.

International Patent Application No. PCT/US2012/028286: International Search Report dated Sep. 5, 2013, pp. 5.

Karlin and Altschul, "Applications and statistics for multiple high-scoring segments in molecular sequences", Jun. 1993, Proc. Natl. Acad. Sci. USA, 90:5873-5877.

Sazinsky et al, "Aglycosylated Immunoglobulin G1 Variants Productively Engage Activating Fc Receptors", Proc. Natl. Acad. Sci. U.S. A., Dec. 23, 2008 105(51):20167-20172.

Wheeler et al., "Mechanisms of Acquired Resistance to Cetuximab: Role of Her (ErbB) Family Members", Oncogene, Jun. 26, 2008, 27(28), 3944-3956.

* cited by examiner

*Primary Examiner* — Sheela J Huff
*Assistant Examiner* — Jessica H Roark
(74) *Attorney, Agent, or Firm* — Baker & Hostetler LLP

(57) ABSTRACT

Disclosed herein are recombinant protein scaffolds for use in producing antigen-binding proteins. Related antigen-binding proteins are also provided herein. In addition, nucleic acids encoding such recombinant protein scaffolds and antigen-binding proteins are also described. Vectors and cells useful for expression of the described proteins are also provided, as are methods of use.

7 Claims, 14 Drawing Sheets

SEQUENCE LISTING

```
<160> NUMBER OF SEQ ID NOS: 45

<210> SEQ ID NO 1
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Tyr Cys Phe Pro Asp Glu Glu Gly Ala Cys Tyr Gly Gly Gly
1               5                   10                  15

Gly Gly Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Leu Glu His His His His His
                245                 250
```

```
<210> SEQ ID NO 2
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Tyr Cys Phe Pro Asp Glu Glu Gly Ala Cys Tyr Gly Gly Gly
1               5                  10                  15

Gly Gly Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Ala Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Leu Glu His His His His His
                245                 250

<210> SEQ ID NO 3
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Tyr Cys Phe Pro Asp Glu Glu Gly Ala Cys Tyr Gly Gly Gly Gly
1               5                  10                  15

Gly Tyr Cys Phe Pro Asp Glu Glu Gly Ala Cys Tyr Gly Gly Gly Gly
            20                  25                  30

Gly Ser Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
```

```
            50                  55                  60
Leu Met Ile Ser Arg Thr Pro Glu Val Thr Cys Val Val Asp Val
 65                  70                  75                  80

Ser His Glu Asp Pro Glu Val Lys Phe Asn Trp Tyr Val Asp Gly Val
                 85                  90                  95

Glu Val His Asn Ala Lys Thr Lys Pro Arg Glu Glu Gln Tyr Asn Ser
                100                 105                 110

Ala Tyr Arg Val Val Ser Val Leu Thr Val Leu His Gln Asp Trp Leu
                115                 120                 125

Asn Gly Lys Glu Tyr Lys Cys Lys Val Ser Asn Lys Ala Leu Pro Ala
            130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
                180                 185                 190

Val Glu Trp Glu Ser Asn Gly Gln Pro Glu Asn Asn Tyr Lys Thr Thr
                195                 200                 205

Pro Pro Val Leu Asp Ser Asp Gly Ser Phe Phe Leu Tyr Ser Lys Leu
210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Leu Glu His His His His His His
                260                 265

<210> SEQ ID NO 4
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Leu Cys Gly Gly Gly Gly Tyr Cys Phe Pro Asp Glu Gly Ala
 1               5                  10                  15

Cys Tyr Gly Gly Gly Gly Ser Asp Lys Thr His Thr Cys Pro Pro
                20                  25                  30

Cys Pro Ala Pro Glu Leu Leu Gly Gly Pro Ser Val Phe Leu Phe Pro
                35                  40                  45

Pro Lys Pro Lys Asp Thr Leu Met Ile Ser Arg Thr Pro Glu Val Thr
 50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
                115                 120                 125

Asn Lys Ala Leu Pro Ala Pro Ile Glu Lys Thr Ile Ser Lys Ala Lys
            130                 135                 140
```

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
            165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
            210                 215                 220

Asn Val Phe Ser Cys Ser Val Met His Glu Ala Leu His Asn His Tyr
225                 230                 235                 240

Thr Gln Lys Ser Leu Ser Leu Ser Leu Glu His His His His His
            245                 250                 255

<210> SEQ ID NO 5
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Leu Cys Gly Gly Gly Gly Tyr Cys Phe Pro Asp Glu Glu Gly Ala
1               5                   10                  15

Cys Tyr Gly Gly Gly Gly Ser Asp Lys Thr His Thr Cys Pro Pro
            20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Ala Tyr Arg Val Val Ser Val Leu Thr Val
            100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
            165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
            210                 215                 220

Asn Val Phe Ser Cys Ser Val Met His Glu Ala Leu His Asn His Tyr
225                 230                 235                 240

Thr Gln Lys Ser Leu Ser Leu Ser Leu Glu His His His His His
            245                 250                 255

```
<210> SEQ ID NO 6
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Leu Cys Gly Gly Gly Ser Tyr Cys Phe Pro Asp Glu Glu Gly Ala
1               5                   10                  15

Cys Tyr Gly Gly Gly Gly Ser Asp Lys Thr His Thr Cys Pro Pro
            20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
        50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Ala Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Leu Glu His His His His His His
                245                 250                 255

<210> SEQ ID NO 7
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Leu Met Gly Gly Gly Gly Tyr Cys Phe Pro Asp Glu Glu Gly
1               5                   10                  15

Ala Cys Tyr Gly Gly Gly Gly Ser Asp Lys Thr His Thr Cys Pro
            20                  25                  30

Pro Cys Pro Ala Pro Glu Leu Leu Gly Gly Pro Ser Val Phe Leu Phe
            35                  40                  45
```

-continued

```
Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Leu Glu His His His His His
                245                 250                 255

His
```

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggaccatgg cttattgctt tccggatgaa gaaggtgcgt gctacggtgg tggcggcggt    60

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gggacatatg tactgtttcc cggacgagga gggcgcatgt tatg    44

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
gagggcgcat gttatggcgg cggtggtggc tattgctttc cggat         45
```

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
gggacatatg ttgtgcggcg gtggtrgcta ttgctttccg gat           43
```

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
gggaccatgg ctttaatggg cggtggtggc tattgcttt               39
```

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
gggactcgag agacagggag aggctctt                            28
```

<210> SEQ ID NO 14
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Leu Glu
225

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Cys Phe Pro Asp Glu Glu Gly Ala Cys Tyr
1               5                   10

<210> SEQ ID NO 16
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(21)
<223> OTHER INFORMATION: Any amino acid and this region may or may not
      be present in its entirety
<220> FEATURE:
<223> OTHER INFORMATION: See specification as filed for detailed
      description of substitutions and preferred embodiments

<400> SEQUENCE: 16

Met Leu Cys Gly Gly Gly Gly Tyr Cys Xaa Xaa Xaa Xaa Xaa Xaa
1               5                   10                  15

Xaa Xaa Xaa Xaa Xaa Cys Tyr Gly Gly Gly Gly Ser Asp Lys Thr
                20                  25                  30

His Thr Cys Pro Pro Cys Pro Ala Pro Glu Leu Leu Gly Gly Pro Ser
            35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
```

```
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
                180                 185                 190

Asn Gly Gln Pro Glu Asn Asn Tyr Lys Thr Thr Pro Pro Val Leu Asp
                195                 200                 205

Ser Asp Gly Ser Phe Phe Leu Tyr Ser Lys Leu Thr Val Asp Lys Ser
        210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Leu Glu His
                245                 250                 255

His His His His His
                260

<210> SEQ ID NO 17
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(21)
<223> OTHER INFORMATION: Any amino acid and this region may or may not
      be present in its entirety
<220> FEATURE:
<223> OTHER INFORMATION: See specification as filed for detailed
      description of substitutions and preferred embodiments

<400> SEQUENCE: 17

Met Leu Cys Gly Gly Gly Gly Tyr Cys Xaa Xaa Xaa Xaa Xaa Xaa
1               5                   10                  15

Xaa Xaa Xaa Xaa Xaa Cys Tyr Gly Gly Gly Gly Ser Asp Lys Thr
                20                  25                  30

His Thr Cys Pro Pro Cys Pro Ala Pro Glu Leu Leu Gly Gly Pro Ser
                35                  40                  45

Val Phe Leu Phe Pro Pro Lys Pro Lys Asp Thr Leu Met Ile Ser Arg
50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Ala Tyr Arg Val Val
                100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
        130                 135                 140

Ile Ser Lys Ala Lys Gly Gln Pro Arg Glu Pro Gln Val Tyr Thr Leu
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
                180                 185                 190

Asn Gly Gln Pro Glu Asn Asn Tyr Lys Thr Thr Pro Pro Val Leu Asp
```

```
            195                 200                 205
Ser Asp Gly Ser Phe Phe Leu Tyr Ser Lys Leu Thr Val Asp Lys Ser
    210                 215                 220
Arg Trp Gln Gln Gly Asn Val Phe Ser Cys Ser Val Met His Glu Ala
225                 230                 235                 240
Leu His Asn His Tyr Thr Gln Lys Ser Leu Ser Leu Ser Leu Glu His
                245                 250                 255
His His His His His
            260

<210> SEQ ID NO 18
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(21)
<223> OTHER INFORMATION: Any amino acid and this region may or may not
      be present in its entirety
<220> FEATURE:
<223> OTHER INFORMATION: See specification as filed for detailed
      description of substitutions and preferred embodiments

<400> SEQUENCE: 18

Met Leu Cys Gly Gly Gly Ser Tyr Cys Xaa Xaa Xaa Xaa Xaa Xaa Xaa
1               5                   10                  15
Xaa Xaa Xaa Xaa Xaa Cys Tyr Gly Gly Gly Gly Ser Asp Lys Thr
            20                  25                  30
His Thr Cys Pro Pro Cys Pro Ala Pro Glu Leu Leu Gly Gly Pro Ser
            35                  40                  45
Val Phe Leu Phe Pro Pro Lys Pro Lys Asp Thr Leu Met Ile Ser Arg
    50                  55                  60
Thr Pro Glu Val Thr Cys Val Val Val Asp Val Ser His Glu Asp Pro
65                  70                  75                  80
Glu Val Lys Phe Asn Trp Tyr Val Asp Gly Val Glu Val His Asn Ala
                85                  90                  95
Lys Thr Lys Pro Arg Glu Glu Gln Tyr Asn Ser Ala Tyr Arg Val Val
            100                 105                 110
Ser Val Leu Thr Val Leu His Gln Asp Trp Leu Asn Gly Lys Glu Tyr
        115                 120                 125
Lys Cys Lys Val Ser Asn Lys Ala Leu Pro Ala Pro Ile Glu Lys Thr
    130                 135                 140
Ile Ser Lys Ala Lys Gly Gln Pro Arg Glu Pro Gln Val Tyr Thr Leu
145                 150                 155                 160
Pro Pro Ser Arg Asp Glu Leu Thr Lys Asn Gln Val Ser Leu Thr Cys
                165                 170                 175
Leu Val Lys Gly Phe Tyr Pro Ser Asp Ile Ala Val Glu Trp Glu Ser
            180                 185                 190
Asn Gly Gln Pro Glu Asn Asn Tyr Lys Thr Thr Pro Pro Val Leu Asp
        195                 200                 205
Ser Asp Gly Ser Phe Phe Leu Tyr Ser Lys Leu Thr Val Asp Lys Ser
    210                 215                 220
Arg Trp Gln Gln Gly Asn Val Phe Ser Cys Ser Val Met His Glu Ala
225                 230                 235                 240
Leu His Asn His Tyr Thr Gln Lys Ser Leu Ser Leu Ser Leu Glu His
                245                 250                 255
```

His His His His His
        260

<210> SEQ ID NO 19
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(22)
<223> OTHER INFORMATION: Any amino acid and this region may or may not
      be present in its entirety
<220> FEATURE:
<223> OTHER INFORMATION: See specification as filed for detailed
      description of substitutions and preferred embodiments

<400> SEQUENCE: 19

Met Ala Leu Met Gly Gly Gly Gly Tyr Cys Xaa Xaa Xaa Xaa Xaa
1               5                   10                  15

Xaa Xaa Xaa Xaa Xaa Xaa Cys Tyr Gly Gly Gly Gly Ser Asp Lys
            20                  25                  30

Thr His Thr Cys Pro Pro Cys Pro Ala Pro Glu Leu Leu Gly Gly Pro
        35                  40                  45

Ser Val Phe Leu Phe Pro Pro Lys Pro Lys Asp Thr Leu Met Ile Ser
    50                  55                  60

Arg Thr Pro Glu Val Thr Cys Val Val Val Asp Val Ser His Glu Asp
65                  70                  75                  80

Pro Glu Val Lys Phe Asn Trp Tyr Val Asp Gly Val Glu Val His Asn
                85                  90                  95

Ala Lys Thr Lys Pro Arg Glu Glu Gln Tyr Asn Ser Thr Tyr Arg Val
            100                 105                 110

Val Ser Val Leu Thr Val Leu His Gln Asp Trp Leu Asn Gly Lys Glu
        115                 120                 125

Tyr Lys Cys Lys Val Ser Asn Lys Ala Leu Pro Ala Pro Ile Glu Lys
    130                 135                 140

Thr Ile Ser Lys Ala Lys Gly Gln Pro Arg Glu Pro Gln Val Tyr Thr
145                 150                 155                 160

Leu Pro Pro Ser Arg Asp Glu Leu Thr Lys Asn Gln Val Ser Leu Thr
                165                 170                 175

Cys Leu Val Lys Gly Phe Tyr Pro Ser Asp Ile Ala Val Glu Trp Glu
            180                 185                 190

Ser Asn Gly Gln Pro Glu Asn Asn Tyr Lys Thr Thr Pro Pro Val Leu
        195                 200                 205

Asp Ser Asp Gly Ser Phe Phe Leu Tyr Ser Lys Leu Thr Val Asp Lys
    210                 215                 220

Ser Arg Trp Gln Gln Gly Asn Val Phe Ser Cys Ser Val Met His Glu
225                 230                 235                 240

Ala Leu His Asn His Tyr Thr Gln Lys Ser Leu Ser Leu Ser Leu Glu
                245                 250                 255

His His His His His His
        260

<210> SEQ ID NO 20
<211> LENGTH: 262
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(22)
<223> OTHER INFORMATION: Any amino acid and this region may or may not
      be present in its entirety
<220> FEATURE:
<223> OTHER INFORMATION: See specification as filed for detailed
      description of substitutions and preferred embodiments

<400> SEQUENCE: 20

Met Ala Leu Met Gly Gly Gly Tyr Cys Xaa Xaa Xaa Xaa Xaa
1               5                  10                  15

Xaa Xaa Xaa Xaa Xaa Xaa Cys Tyr Gly Gly Gly Gly Ser Asp Lys
                20                  25                  30

Thr His Thr Cys Pro Pro Cys Pro Ala Pro Glu Leu Leu Gly Gly Pro
            35                  40                  45

Ser Val Phe Leu Phe Pro Pro Lys Pro Lys Asp Thr Leu Met Ile Ser
        50                  55                  60

Arg Thr Pro Glu Val Thr Cys Val Val Val Asp Val Ser His Glu Asp
65                  70                  75                  80

Pro Glu Val Lys Phe Asn Trp Tyr Val Asp Gly Val Glu Val His Asn
                85                  90                  95

Ala Lys Thr Lys Pro Arg Glu Glu Gln Tyr Asn Ser Ala Tyr Arg Val
            100                 105                 110

Val Ser Val Leu Thr Val Leu His Gln Asp Trp Leu Asn Gly Lys Glu
        115                 120                 125

Tyr Lys Cys Lys Val Ser Asn Lys Ala Leu Pro Ala Pro Ile Glu Lys
130                 135                 140

Thr Ile Ser Lys Ala Lys Gly Gln Pro Arg Glu Pro Gln Val Tyr Thr
145                 150                 155                 160

Leu Pro Pro Ser Arg Asp Glu Leu Thr Lys Asn Gln Val Ser Leu Thr
                165                 170                 175

Cys Leu Val Lys Gly Phe Tyr Pro Ser Asp Ile Ala Val Glu Trp Glu
            180                 185                 190

Ser Asn Gly Gln Pro Glu Asn Asn Tyr Lys Thr Thr Pro Pro Val Leu
        195                 200                 205

Asp Ser Asp Gly Ser Phe Phe Leu Tyr Ser Lys Leu Thr Val Asp Lys
    210                 215                 220

Ser Arg Trp Gln Gln Gly Asn Val Phe Ser Cys Ser Val Met His Glu
225                 230                 235                 240

Ala Leu His Asn His Tyr Thr Gln Lys Ser Leu Ser Leu Ser Leu Glu
                245                 250                 255

His His His His His His
            260

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Gly Ser
1               5
```

<210> SEQ ID NO 22
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Gly Gly Pro Ser Val Phe Leu Phe Pro Pro Lys Pro Lys Asp Thr
1               5                   10                  15

Leu Met Ile Ser Arg Thr Pro Glu Val Thr Cys Val Val Val Asp Val
            20                  25                  30

Ser His Glu Asp Pro Glu Val Lys Phe Asn Trp Tyr Val Asp Gly Val
        35                  40                  45

Glu Val His Asn Ala Lys Thr Lys Pro Arg Glu Glu Gln Tyr Asn Ser
    50                  55                  60

Thr Tyr Arg Val Val Ser Val Leu Thr Val Leu His Gln Asp Trp Leu
65                  70                  75                  80

Asn Gly Lys Glu Tyr Lys Cys Lys Val Ser Asn Lys Ala Leu Pro Ala
                85                  90                  95

Pro Ile Glu Lys Thr Ile Ser Lys
            100

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Leu Glu
            100                 105

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Cys Asp Gly Phe Tyr Ala Cys Tyr Met Asp Val
1               5                   10

```
<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Cys Asp Gly Phe Tyr Ala Cys Tyr Met Asp Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Cys Asp Gly Phe Gly Gly Cys Tyr Met Asp Val
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Cys Trp Ser Gln Tyr Leu Cys Tyr
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Cys Asp Glu His Phe Cys Tyr
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Cys Glu Ile Glu Phe Cys Tyr Leu Ile Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Phe Cys Ile Tyr Ser Gly Ser Thr Cys Tyr
1               5                   10

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Pro Cys Pro Ile Asn Cys Thr His Ser Cys Val Asp Leu Asp Asp Lys
1               5                   10                  15

Gly Cys Pro Ala Glu Gln Arg Ala Ser Pro Leu Thr Ser Ile
            20                  25                  30

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Cys Pro Ile Trp Lys Phe Pro Asp Glu Glu Cys Tyr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Cys Gly Tyr Ser Ser Thr Ser Tyr Cys Phe Val Met Asp
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Cys Ala Ser Arg Asp Tyr Asp Tyr Asp Gly Arg Cys Tyr Phe Asp
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Cys Thr Arg Gly Tyr Ser Ser Thr Ser Tyr Cys Tyr Ala Met Asp
1               5                   10                  15
```

-continued

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Cys Met Glu Glu Ser Gly Gly Asn Tyr Cys Tyr
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Cys Ala Leu Arg Gly Gly Val Tyr Trp Pro Cys Tyr
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Cys Ala Leu Thr Tyr Tyr Asp Tyr Glu Cys Phe Ala Tyr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Cys Tyr Ile Cys Glu Val Glu Asp Gln Cys Tyr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Cys Val Val Gln Asp Trp Gly His His Arg Cys Thr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Cys Phe Thr Ala Ser Glu Asn His Cys Tyr
1               5                   10

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Cys Pro Ala Leu Val Thr Tyr Asn Thr Asp Thr Phe Glu Ser Met
1               5                   10                  15

Pro Asn Pro Glu Gly Arg Cys Tyr
            20

<210> SEQ ID NO 43
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser Gly Phe
                85                  90                  95

Leu Phe Ala Glu Ile Val Ser Ile Phe Val Leu Ala Val Gly Val Tyr
            100                 105                 110

Phe Ile Ala Gly Gln Asp Gly Val Arg Gln Ser Arg Ala Ser Asp Lys
        115                 120                 125

Gln Thr Leu Leu Pro Asn Asp Gln Leu Tyr Gln Pro Leu Lys Asp Arg
    130                 135                 140

Glu Asp Asp Gln Tyr Ser His Leu Gln Gly Asn Gln Leu Arg Arg Asn
145                 150                 155                 160

<210> SEQ ID NO 44
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

```
Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp Val Met Ser Val Ala Thr Ile Val
                100                 105                 110

Ile Val Asp Ile Cys Ile Thr Gly Gly Leu Leu Leu Leu Val Tyr Tyr
            115                 120                 125

Trp Ser Lys Asn Arg Lys Ala Lys Ala Lys Pro Val Thr Arg Gly Ala
        130                 135                 140

Gly Ala Gly Gly Arg Gln Arg Gly Gln Asn Lys Glu Arg Pro Pro Pro
145                 150                 155                 160

Val Pro Asn Pro Asp Tyr Glu Pro Ile Arg Lys Gly Gln Arg Asp Leu
                165                 170                 175

Tyr Ser Gly Leu Asn Gln Arg Arg Ile
            180                 185

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 45

His His His His His His
1               5
```

ANTIBODY-LIKE PROTEINS FOR THERAPEUTIC AND DIAGNOSTIC USE

CROSS REFERENCE TO RELATED APPLICATIONS

This application is the National Stage of International Application No. PCT/US2012/028286, filed Mar. 8, 2012, which claims the benefit of U.S. Provisional Application No. 61/450,435 filed Mar. 8, 2011, the disclosures of which are incorporated herein by reference in their entireties for any and all purposes.

GOVERNMENT RIGHTS

The subject matter disclosed herein was made with government support under award/contract/grant No. CA055306 awarded by the National Institutes of Health. The Government hasa certain rights in the herein disclosed subject matter.

SEQUENCE LISTING

The instant application contains a Sequence Listing which has been submitted in ASCII format via EFS-Web and is hereby incorporated by reference in its entirety. Said ASCII copy, created on Mar. 24, 2015, is named 103241.005883-X5822_SL.txt and is 44,371 bytes in size.

TECHNICAL FIELD

The present invention relates to peptide-Fc fusion proteins that can be used in detection assays, as therapeutics or as substitutes for monoclonal antibodies in other applications.

BACKGROUND

Since hybridoma technology enabled long-lived hybridoma production of monoclonal antibodies in the mid-1970's, scientist and clinicians have been trying to harvest their therapeutic potential to treat diseases. Over the years, science has pushed back the frontiers of antibody technology, allowing for the development of chimeric antibodies, humanized antibodies, and immunologically functional antibody fragments, such as Fabs and diabodies. Today, there are numerous antibody therapeutics used to treat diseases such as cancer, infectious diseases, and autoimmune disorders, just to name a few. In addition to existing therapeutics, more are on the horizon and the scientific community is working feverishly to develop new and/or more effective antibody-based therapeutics.

While antibody therapeutics have proven successful in recent years, with at least 25 such therapeutics having gained FDA approval, they are not without drawbacks. Some drawbacks to antibodies include their large size (approximately 150 kD) and that they often require proper post-translational processing. The large size of antibodies can reduce their ability to target certain diseases, such as cancer or neurological disorders, which may require crossing the blood-brain barrier. The fact that many antibodies require proper post-translational processing by a eukaryotic cell often requires that antibody therapeutics be produced in, and subsequently purified from, mammalian cell culture, which can hinder total antibody production and increase production costs, relative to proteins produced in bacteria.

To overcome some of the drawbacks of antibodies, non-antibody synthetic proteins have been developed. Some examples of non-antibody synthetic proteins include antibody fragments, such as Fabs, scFvs, diabodies, Affibodies®, and Nanobodies®, to name a few. Proteins such as these, while smaller than antibodies and useful for some applications, often do not have the ability to interact with antibody receptors, such as the Fc receptor, expressed by immune effector cells, which can enhance the activity of the immune system.

To address some of the shortcomings of antibodies and non-antibody synthetic proteins, disclosed herein are antigen-binding protein constructs that incorporate all or part of an antibody Fc domain.

SUMMARY

Described herein are protein scaffolds for use in producing antigen-binding proteins. A variety of protein scaffolds are described, as are a variety of functional attributes or characteristics that can be associated with the described protein scaffolds. Several of the disclosed protein scaffolds are made of at least one protein scaffold or framework segment that can be linked to at least one antigen-specific polypeptide sequence, known as an antigen-specific peptide, to form an antigen-binding protein. The scaffold proteins described herein can also be modified to bind, or enhancing binding, to the fragment crystallizable (Fc) receptors. In addition, some of the scaffold protein segments may inherently possess these, or other, desired functional characteristics, which also allows them to be attached to other antigen-specific proteins to confer this activity. Some of the antigen-binding proteins resulting from the combination of the described scaffold protein constructs and an antigen-specific peptide that are described herein have the ability to bind a particular antigen and an Fc receptor in addition to having an attached detectable label. Also disclosed are polynucleotides encoding the described protein scaffolds or exemplary antigen-binding proteins, vectors encoding the described scaffolds or exemplary antigen-binding proteins, cells transformed with the disclosed vectors, and methods of treating, diagnosing, or preventing disease using the described antigen-binding proteins, and methods of detecting antigens of interest using the described antigen-binding proteins.

One embodiment of the protein scaffolds described herein can be all or a portion of a heavy chain constant region 2 ($C_H2$) of an antibody, for example, SEQ ID NO:22. The described $C_H2$ region can be linked or combined with at least one antigen-specific peptide to form an antigen-binding protein. In one embodiment, the antigen-binding protein includes the $C_H2$ scaffold linked to an antigen-specific peptide, such as the S22 peptide (SEQ ID NO:15) derived from human epidermal growth factor receptor 2 (HER2) receptor, to create an antigen-binding protein that is able to bind HER2, epidermal growth factor receptor (EGFR), or human epidermal growth factor receptor 3 (HER3). In another embodiment this antigen-binding protein, or an analogous antigen-binding protein specific for a different antigen, can include a detectable label, for example, an epitope tag, a fluorophore, a radio isotope, or an enzyme. It should be noted that many embodiments of the antigen-binding proteins described herein are exemplified using the antigen-specific peptide S22; however, any of the antigen-specific peptides known to those of skill in the art, can be used to produce antigen-binding proteins using the protein scaffolds described herein. Antigen-specific peptides that may be used with the described protein scaffolds to produce antigen-binding proteins include those associated with SEQ ID NOs:24, 25, 26, 27, 28, 29, 30, 31, 32, 33, 34, 35, 36, 37, 38, 39, 40, 41, 42, 43, or 44.

The described $C_H2$ region can also be conjugated to a corresponding $C_H3$ region (such as that exemplified by SEQ ID NO:23) and an antigen-specific peptide, to form an antigen-binding protein that includes, or approximates, the Fc domain of an antibody. One embodiment of such an antigen-binding protein can include the S22 peptide fused to a $C_H2$ region, which is also attached to a $C_H3$ region. One such embodiment is provided by the amino acid sequence of, or substantially similar to, SEQ ID NO:1. The $C_H2$ and $C_H3$ regions described herein can be obtained from any adequate antibody having such regions, for example IgG, IgD, IgM, IgE, IgA, or IgY, to name several. The sources of such antibodies can vary also, such that these regions could be obtained from a human antibody, murine antibody, primate antibody, rodent antibody, avian antibody or other such vertebrate source. In some embodiments, a particular subtype of antibody may be used, such as IgG1. In other embodiments, the $C_H2$ and $C_H3$ regions maybe mixed. For example, a $C_H2$ from a human IgG1 antibody could be joined with a $C_H3$ region of a murine IgG2 antibody. Other such combinations analogous to this example would be apparent to those skilled in the art. It should be noted that many embodiments of the antigen-binding proteins described herein are often exemplified using the antigen-specific peptide S22; however, any of the antigen-specific peptides known to those of skill in the art, can be used to produce antigen-binding proteins using the protein scaffolds described herein.

The described protein scaffolds and antigen-binding proteins can also include altered amino acid sequences that provide an enhanced protein function or reduce one or more undesirable property of the construct. These alterations may be achieved by a number of techniques known in the art, such as genetic engineering to alter the resulting amino acid sequence of the antigen-binding protein, chemical modification of the antigen-binding protein, or the addition functional peptides or motifs. In one embodiment, the described $C_H2$ region, or Fc domain, may be altered to include one of more mutated amino acid residues. For example, residue 299 of the $C_H2$ domain (or the amino acid corresponding to this residue in a related antigen-binding protein) may be modified to be a different amino acid. In one embodiment, residue 299 of the $C_H2$ domain is changed from threonine to alanine. It will be understood by those skilled in the art that amino acid 299 of the $C_H2$ region will not necessarily appear at position 299 in instances where a $C_H2$ region is modified or incorporated to a larger scaffold or antigen-binding protein. Accordingly, in some embodiments, a residue of a protein-binding protein construct incorporating a $C_H2$ region may be modified to encode a residue other than threonine at the amino acid corresponding to residue 299 of the $C_H2$ region. For example, in one embodiment, a mutation of the residue corresponding to amino acid 299 of the $C_H2$ region may occur at position 322 for an antigen-binding protein construct where the S22 peptide is linked to a $C_H2$ region, since the addition of the S22 peptide adds N-terminal residues to the $C_H2$ region. While this example is provided in the context of the $C_H2$ peptide, other antigen specific peptides could alter the positioning of the $C_H2$ residues in an analogous manner. Other scaffolds provided herein include LFcG7 (SEQ ID NO:16), LFcT322AG7 (SEQ ID NO:17), LFcT322AS7 (SEQ ID NO:18), and MFcG7 (SEQ ID NO:19) and MFcT322AG7 (SEQ ID NO:20).

Also disclosed herein are the amino acid sequences for a number of the scaffolds and antigen-binding proteins described, as such, corresponding nucleotide sequences encoding these scaffolds and antigen-binding proteins will be apparent to those skilled in the art. Vectors used to express these polynucleotide sequences encoding the disclosed amino acid sequences are also provided. For the sake of brevity, only a limited number of vectors having polynucleotide sequences capable of encoding the described constructs are provided; however, alternative vector and polynucleotide combinations for expressing the disclosed antigen-binding proteins will be apparent to those with sufficient skill in the art to understand the degeneracy of the genetic code. Additionally, it is fully contemplated that the disclosed vectors can be used to transform prokaryotic and/or eukaryotic cells to facilitate expression of the described antigen-binding proteins. In some embodiments the described vectors are used to facilitate protein expression in bacteria, such as *E. coli*. While any *E. coli* strain can be used to express the proteins described herein, some preferred strains include: BL21 (DE3), BL21-CodonPlus® (DE3)-RP, BL21-CodonPlus® (DE3)-RIL, BL21-(DE3)-pLysS (Stratagene). Eukaryotic cells can also be used with the described vectors to facilitate protein expression. While those of skill in the art will recognize that a wide variety of eukaryotic cells will be suitable for this purpose, some preferred embodiments include mammalian cells and insect cells. For example, in one embodiment Chinese hamster ovary (CHO) cells can be used with the described vectors to facilitate expression of the protein constructs provided herein. In alternative embodiments, insect cells, such as Sf9 cells or S2 cells, can be used to with the described vectors to facilitate expression of the protein constructs provided herein. Furthermore, those of skill in the art will understand that alternative vectors, not expressly disclosed herein, can be used for the same purpose of expressing, or replicating nucleic acids encoding, the described antigen-binding proteins.

Also described herein are compositions containing an antigen-binding protein and a pharmaceutically acceptable carrier. Such compositions can be used to administer the described antigen-binding proteins to a subject or store or to maintain the described antigen-binding proteins. Any of the described antigen-binding proteins can be used to produce such compositions, which may include more than one of the disclosed antigen-binding proteins. In addition, such compositions can include other agents, such as therapeutic agents, preservatives, antimicrobial agents, and the like.

Methods of using the described scaffolds, or antigen-binding proteins, are also provided. For example, antigen-binding proteins derived from the scaffolds disclosed herein may be used to treat or prevent disease in a subject. The described methods of treating or preventing disease can be used to administer compositions, having antigen-binding proteins derived from the described scaffolds, to a subject in need of such treatment. Also disclosed are methods for detecting an antigen of interest using antigen-binding proteins derived from the scaffolds disclosed herein. Such methods are applicable to antigen detection in a subject, in a sample obtained from a subject, or in vitro.

DETAILED DESCRIPTION OF ILLUSTRATIVE EMBODIMENTS

Figure 1:
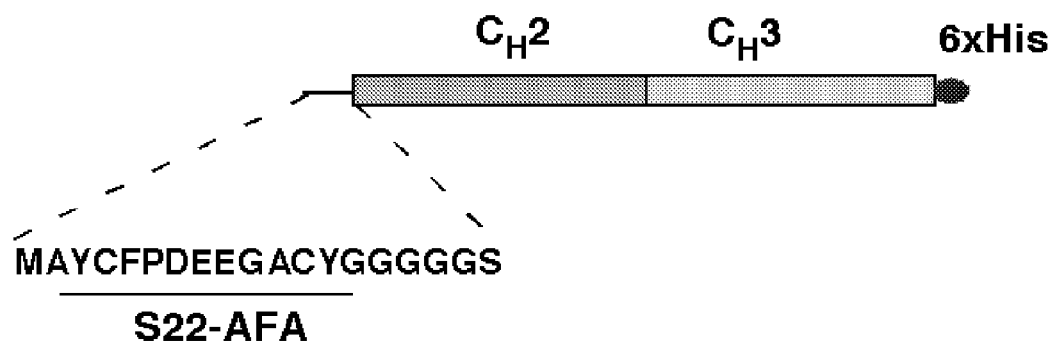
FIG. 1 provides a schematic representation of the S22-Fc antigen-binding protein construct. Amino acid sequences for the S22 peptide and glycine-serine linker are shown (residues 1-19 of SEQ ID NO:1).

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

As used herein, the term "cytotoxic" or "cytostatic" agent refers to an agent that inhibits the biological processes of a cell, or reduces the viability or proliferative potential of a cell. Cytotoxic or cytostatic agents can function in a variety of ways, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Chemotherapeutic agents include, but are not limited to, synthetic compounds, natural and recombinant bacterial toxins, natural and recombinant fungal toxins, natural and recombinant plant toxins, fissionable nuclides, and radionuclides. Specific examples of chemotherapeutic agents include, but are not limited to, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, lead-212, bismuth-212, astatine-211, iodine-131, scandium-47, rhenium-186, rhenium-188, yttrium-90, iodine-123, iodine-124, iodine-125, bromine-77, indium-111, boron-10, actinide, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, 5-fluorouracil, cyclophosphamide and certain cytokines such as TNF-alpha and TNF-beta.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Substantially the same" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using mBLAST algorithm (Altschul et al. (1990) Proc. Natl. Acad. Sci. USA 87:2264-8; Karlin and Altschul (1993) Proc. Natl. Acad. Sci. USA 90:5873-7).

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

A cell has been "transformed" or "transfected" by exogenous or heterologous nucleic acids such as DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Biomolecules" include proteins, polypeptides, nucleic acids, lipids, monosaccharides, polysaccharides, and all fragments, analogs, homologs, conjugates, and derivatives thereof.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

The terms "treating" or "treatment" can refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters.

"Effective amount" and "therapeutically effective amount" are used interchangeably herein, and refer to an amount of an antibody, antigen-binding fragment, or antibody composition, as described herein, effective to achieve a particular biological or therapeutic result such as, but not limited to, biological or therapeutic results disclosed, described, or exemplified herein. A therapeutically effective amount of the antibody or antigen-binding fragment thereof may vary according to factors such as the disease state, age, sex, and weight of the individual, and the ability of the antibody or antigen-binding fragment thereof to elicit a desired response in the individual. Such results may include, but are not limited to, the treatment of cancer, as determined by any means suitable in the art.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

"Antibody" refers to all isotypes of immunoglobulins (IgG, IgA, IgE, IgM, IgD, and IgY) including various monomeric and polymeric forms of each isotype, unless otherwise specified.

"Antibody fragments" comprise a portion of a full length antibody, generally the antigen binding or variable region thereof, such as Fab, Fab', F(ab') 2, and Fv fragments; diabodies; linear antibodies; single-chain antibody molecules; and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the V H and V L domains of antibody, wherein these domains are present in a single polypeptide chain. Generally, the Fv polypeptide further comprises a polypeptide linker between the V H and V L domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

"Scaffold" refers to a recombinant polypeptide structure that can provide a framework to which another protein or polypeptide may be linked, or fused, to allow for increased stability of the protein or peptide or to place the protein or peptide in a more preferred conformation, or form, to mediate a desired biological activity.

"Linked" in the context of a scaffold or antigen-binding protein means "connected to" either directly or indirectly. Indirect linkage can be mediated by a polypeptide linker such as poly-glycine or a glycine-serine polypeptide, for example, GGGGGS (SEQ ID NO:21). Other such linkers are known in the art and should be considered to be encompassed by this term.

Described herein are protein scaffolds for use in producing antigen-binding proteins. A variety of protein scaffolds are described, as are a variety of functional attributes or characteristics that can be associated with the described protein scaffolds. Several of the disclosed protein scaffolds are made of at least one protein scaffold or framework segment that can be linked to at least one antigen-specific polypeptide sequence, known as an antigen-specific peptide, to form an antigen-binding protein. The scaffold proteins described herein can also be modified to bind, or enhancing binding, to the fragment crystallizable (Fc) receptors. In addition, some of the scaffold protein segments may inherently possess these, or other, desired functional characteristics, which also allows them to be attached to other antigen-specific proteins to confer this activity. Some of the antigen-binding proteins resulting from the combination of the described scaffold protein constructs and an antigen-specific peptide that are described herein have the ability to bind a particular antigen and an Fc receptor in addition to having an attached detectable label. Also disclosed are polynucleotides encoding the described protein scaffolds or exemplary antigen-binding proteins, vectors encoding the described scaffolds or exemplary antigen-binding proteins, cells transformed with the disclosed vectors, and methods of treating, diagnosing, or preventing disease using the described antigen-binding proteins, and methods of detecting antigens of interest using the described antigen-binding proteins.

The antigen-binding proteins exemplified herein have been made with the antigen-specific peptide S22, which allows for comparative studies between the scaffolds, and antibodies or antibody fragments that have similar antigen specificity. This practical aspect of the present disclosure should not be considered to limit the scaffolds provided herein for use with only S22, as it should be apparent that these scaffolds, as described in Table 1, can be used with a wide variety of antigen-specific peptides. While the particular amino acid sequences provided represent the specific embodiments exemplified herein, it should be understood that certain amino acid substitutions, deletions, or additions could be made to the described sequences that would not alter the function of the described scaffolds or antigen-binding proteins. Therefore, it is contemplated that scaffolds or antigen-binding proteins having at least 80% homology to those described herein are within the scope of the disclosed subject matter. Furthermore, it is contemplated that scaffolds or antigen-binding proteins having at least 85% homology to those described herein are within the scope of the disclosed subject matter. In addition, it is contemplated that scaffolds or antigen-binding proteins having at least 90% homology to those described herein are within the scope of the disclosed subject matter. Moreover, it is contemplated that scaffolds or antigen-binding proteins having at least 95% homology to those described herein are within the scope of the disclosed subject matter.

One embodiment of the protein scaffolds described herein is a heavy chain constant region 2 ($C_H2$) of an antibody, such as SEQ ID NO:22. The described $C_H2$ region can be linked or combined with at least one antigen-specific peptide to form an antigen-binding protein. In one embodiment, the antigen-binding protein includes the $C_H2$ scaffold linked to an antigen-specific peptide, such as the S22 peptide (SEQ ID NO:15) derived from HER2, to create an antigen-binding protein that is able to bind HER2, EGFR, or HER3. In another embodiment this antigen-binding protein, or an analogous antigen-binding protein specific for a different antigen, can include a detectable label, for example, an epitope tag, a fluorophore, a radio isotope, or an enzyme. It should be noted that many embodiments of the antigen-binding proteins described herein are exemplified using the antigen-specific peptide S22; however, any of the antigen-specific peptides known to those of skill in the art, can be used to produce antigen-binding proteins using the protein scaffolds described herein.

The described $C_H2$ region can also be conjugated to a corresponding $C_H3$ region and an antigen-specific peptide, to form an antigen-binding protein. In some embodiments an antigen-binding protein with a $C_H2$ and $C_H3$ domain can include, or approximate, an Fc domain of an antibody. In some embodiments, the $C_H2$ region may include one or more amino acid residues associated with the hinge region of an antibody. For example, a $C_H2$ having hinge region amino acids may be used to allow the $C_H2$ region to better approximate the $C_H2$ region of an Fc domain. Such $C_H2$ region may be used with or without a $C_H3$ region to approximate an Fc domain. In one embodiment of the antigen-binding proteins described herein the S22 peptide is fused to all, or part of, the hinge region of an antibody preceding a $C_H2$ region, which in turn is attached to a $C_H3$ region. One embodiment of the antigen-binding proteins described herein can include the S22 peptide fused to a $C_H2$ region, which is also attached to a $C_H3$ region. One such embodiment is provided by the amino acid sequence of, or substantially similar to, SEQ ID NO:1. The $C_H2$ and $C_H3$ regions described herein can be obtained from any adequate antibody having such regions, for example IgG, IgD, IgM, IgE, IgA, IgY and any subtype thereof, to name several. The sources of such antibodies can vary also, such that these regions could be obtained from a human antibody, murine antibody, primate antibody, rodent antibody, avian antibody or other such vertebrate source. In some embodiments, a particular subtype of antibody may be used, such as IgG1. In other embodiments, the $C_H2$ and $C_H3$ regions maybe mixed. For example, a $C_H2$ from a human IgG1 antibody could be joined with a $C_H3$ region of a murine IgG2 antibody. Other such combinations analogous to this example would be apparent to those skilled in the art. It should be noted that many embodiments of the antigen-binding proteins described herein are often exemplified using the antigen-specific peptide S22; however, any of the antigen-specific peptides known to those of skill in the art, can be used to produce antigen-binding proteins using the protein scaffolds described herein.

In some embodiments, the described antigen-specific binding protein constructs may include amino acid resides that precede the antigen-specific peptide of the construct. Such residues may allow for increased protein stability, enhanced half-life, altered antigen binding, increased antigen affinity, or other such properties. In some aspects as many as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues may precede the antigen-specific peptide. In other embodiments methionine alone (M) may precede the antigen-specific peptide, such as provided in SEQ ID NO:3. In other embodiments the amino acids MA may precede the antigen-specific peptide, such as provided in residues 1 and 2 of SEQ ID NO:1. In one embodiments the amino acids MLCGGGG (residues 1-7 of SEQ ID NO: 4) may precede the antigen-specific peptide, such as provided in residues 1-7 of SEQ ID NO:4. In one embodiment the amino acids MLCGGGS (residues 1-7 of SEQ ID NO: 6) may precede the antigen-specific peptide, such as provided in residues 1-7 of SEQ ID NO:6. In one embodiments the amino acids MALMGGGG (residues 1-8 of SEQ ID NO: 7) may precede the antigen-specific peptide, such as provided in residues 1-8 of SEQ ID NO:7.

The described protein scaffolds and antigen-binding proteins can also include altered amino acid sequences that provide an enhanced protein function or reduce one or more undesirable property of the construct. These alterations may be achieved by a number of techniques known in the art, such as genetic engineering to alter the resulting amino acid sequence of the antigen-binding protein, chemical modification of the antigen-binding protein, or the additional functional peptides or motifs. In one embodiment, the described $C_H2$ region, or Fc domain, may be altered to include one of more mutated amino acid residues. For example, residue 299 of the $C_H2$ domain (or the amino acid corresponding to this residue in a related antigen-binding protein) may be modified to be a different amino acid. A modification of this sort may include mutating the native amino acid to be any other amino acid residue, such as alanine, arginine, asparagine, aspartic acid, cysteine, glutamine, glutamic acid, glycine, histidine, isoleucine, leucine, lysine, methionine, phenylalanine, proline, serine, tryptophan, tyrosine, or valine. In one embodiment, residue 299 of the $C_H2$ domain is changed from threonine to alanine. It will be understood by those skilled in the art that amino acid 299 of the $C_H2$ region will not necessarily appear at position 299 in instances where a $C_H2$ region is modified or incorporated to a larger scaffold or antigen-binding protein. Accordingly, in some embodiments, a residue of a protein-binding protein construct incorporating a $C_H2$ region may be modified to encode a residue other than threonine at the amino acid corresponding to residue 299 of the $C_H2$ region. For example, in one embodiment, a mutation of the residue corresponding to amino acid 299 of the $C_H2$ region may occur at position 322 for an antigen-binding protein construct where the S22 peptide is linked to a $C_H2$ region, since the addition of the S22 peptide adds N-terminal residues to the $C_H2$ region. It should be noted that the numerical values noted for the described $C_H2$ mutations are derived from the position of these amino acid residues in a full length IgG1 molecule and not their position in the context of the described scaffolds or antigen-binding proteins. To better exemplify this, the amino acid residue of the T322A mutation of SEQ ID NO:17 is underlined in Table 1. While this example is provide in the context of the $C_H2$ peptide, other antigen specific peptides could alter the positioning of the $C_H2$ residues in an analogous manner. Other scaffolds provided herein include LFcG7 (SEQ ID NO:16), LFcT322AG7 (SEQ ID NO:17), LFcT322AS7 (SEQ ID NO:18), and MFcG7 (SEQ ID NO:19) and MFcT322AG7 (SEQ ID NO:20). The amino acid sequences for each of these scaffolds shown in Table 1 includes a sequence of 12 "X" positions representing an antigen-specific peptide. While these placeholders are composed of 12 "X" positions, it should be understood that the antigen-specific peptide associated with the scaffold may contain a greater or lesser number of amino acid residues, such as SEQ ID NO:15 or any of SEQ ID NOs:24-44.

TABLE 1

| Described Sequences | | |
|---|---|---|
| SEQ ID NO. | Protein | Exemplary Amino Acid Sequence |
| 1 | S22-Fc | MAYCFPDEEGACYGGGGGSDKTHTCPPCPAPELLG<br>GPSVFLFPPKPKDTLMISRTPEVTCVVVDVSHEDPE<br>VKFNWYVDGVEVHNAKTKPREEQYNSTYRVVSVL<br>TVLHQDWLNGKEYKCKVSNKALPAPIEKTISKAKG<br>QPREPQVYTLPPSRDELTKNQVSLTCLVKGFYPSDI<br>AVEWESNGQPENNYKTTPPVLDSDGSFFLYSKLTV<br>DKSRWQQGNVFSCSVMHEALHNHYTQKSLSLSLE<br>HHHHHH |
| 2 | S22-FcT322A | MAYCFPDEEGACYGGGGGSDKTHTCPPCPAPELLG<br>GPSVFLFPPKPKDTLMISRTPEVTCVVVDVSHEDPE<br>VKFNWYVDGVEVHNAKTKPREEQYNSAYRVVSVL<br>TVLHQDWLNGKEYKCKVSNKALPAPIEKTISKAKG<br>QPREPQVYTLPPSRDELTKNQVSLTCLVKGFYPSDI<br>AVEWESNGQPENNYKTTPPVLDSDGSFFLYSKLTV<br>DKSRWQQGNVFSCSVMHEALHNHYTQKSLSLSLE<br>HHHHHH |
| 3 | S22-FcT322A#4 | MYCFPDEEGACYGGGGGYCFPDEEGACYGGGGGS<br>DKTHTCPPCPAPELLGGPSVFLFPPKPKDTLMISRTP<br>EVTCVVVDVSHEDPEVKFNWYVDGVEVHNAKTKP<br>REEQYNSAYRVVSVLTVLHQDWLNGKEYKCKVSN<br>KALPAPIEKTISKAKGQPREPQVYTLPPSRDELTKNQ<br>VSLTCLVKGFYPSDIAVEWESNGQPENNYKTTPPVL<br>DSDGSFFLYSKLTVDKSRWQQGNVFSCSVMHEALH<br>NHYTQKSLSLSLEHHHHHH |
| 4 | LS22FcG7 | MLCGGGGYCFPDEEGACYGGGGGSDKTHTCPPCP<br>APELLGGPSVFLFPPKPKDTLMISRTPEVTCVVVDV<br>SHEDPEVKFNWYVDGVEVHNAKTKPREEQYNSTY<br>RVVSVLTVLHQDWLNGKEYKCKVSNKALPAPIEKT<br>ISKAKGQPREPQVYTLPPSRDELTKNQVSLTCLVKG<br>FYPSDIAVEWESNGQPENNYKTTPPVLDSDGSFFLY<br>SKLTVDKSRWQQGNVFSCSVMHEALHNHYTQKSL<br>SLSLEHHHHHH |
| 5 | LS22FcT322AG7<br>also noted as<br>S22-FcT322A#2 | MLCGGGGYCFPDEEGACYGGGGGSDKTHTCPPCP<br>APELLGGPSVFLFPPKPKDTLMISRTPEVTCVVVDV<br>SHEDPEVKFNWYVDGVEVHNAKTKPREEQYNSAY<br>RVVSVLTVLHQDWLNGKEYKCKVSNKALPAPIEKT<br>ISKAKGQPREPQVYTLPPSRDELTKNQVSLTCLVKG<br>FYPSDIAVEWESNGQPENNYKTTPPVLDSDGSFFLY<br>SKLTVDKSRWQQGNVFSCSVMHEALHNHYTQKSL<br>SLSLEHHHHHH |
| 6 | LS22FcT322AS7 | MLCGGGSYCFPDEEGACYGGGGGSDKTHTCPPCPA<br>PELLGGPSVFLFPPKPKDTLMISRTPEVTCVVVDVS<br>HEDPEVKFNWYVDGVEVHNAKTKPREEQYNSAYR<br>VVSVLTVLHQDWLNGKEYKCKVSNKALPAPIEKTI<br>SKAKGQPREPQVYTLPPSRDELTKNQVSLTCLVKGF<br>YPSDIAVEWESNGQPENNYKTTPPVLDSDGSFFLYS<br>KLTVDKSRWQQGNVFSCSVMHEALHNHYTQKSLS<br>LSLEHHHHHH |

TABLE 1 -continued Described Sequences

| SEQ ID NO. | Protein | Exemplary Amino Acid Sequence |
|---|---|---|
| 7 | MS22FcG7 | MALMGGGGYCFPDEEGACYGGGGGSDKTHTCPPC PAPELLGGPSVFLFPPKPKDTLMISRTPEVTCVVVD VSHEDPEVKFNWYVDGVEVHNAKTKPREEQYNST YRVVSVLTVLHQDWLNGKEYKCKVSNKALPAPIE KTISKAKGQPREPQVYTLPPSRDELTKNQVSLTCLV KGFYPSDIAVEWESNGQPENNYKTTPPVLDSDGSFF LYSKLTVDKSRWQQGNVFSCSVMHEALHNHYTQK SLSLSLEHHHHHH |
| 8 | S22_s | GGGACCATGGCTTATTGCTTTCCGGATGAAGAAG GTGCGTGCTACGGTGGTGGCGGCGGT |
| 9 | 2S22 | GGGACATATGTACTGTTTCCCGGACGAGGAGGGC GCATGTTATG |
| 10 | 2ndL | GAGGGCGCATGTTATGGCGGCGGTGGTGGCTATT GCTTTCCGGAT |
| 11 | LS22 | GGGACATATGTTGTGCGGCGGTGGTRGCTATTGC TTTCCGGAT |
| 12 | MS22 | GGGACCATGGCTTTAATGGGCGGTGGTGGCTATT GCTTT |
| 13 | CH3rXho | GGGACTCGAGAGACAGGGAGAGGCTCTT |
| 14 | Fc | DKTHTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSLE |
| 15 | S22 peptide | YCFPDEEGACY |
| 16 | LFcG7 | MLCGGGGYCXXXXXXXXXXXXCYGGGGGSDKTH TCPPCPAPELLGGPSVFLFPPKPKDTLMISRTPEVTC VVVDVSHEDPEVKFNWYVDGVEVHNAKTKPREEQ YNSTYRVVSVLTVLHQDWLNGKEYKCKVSNKALP APIEKTISKAKGQPREPQVYTLPPSRDELTKNQVSLT CLVKGFYPSDIAVEWESNGQPENNYKTTPPVLDSD GSFFLYSKLTVDKSRWQQGNVFSCSVMHEALHNH YTQKSLSLSLEHHHHHH |
| 17 | LFcT322AG7 | MLCGGGGYCXXXXXXXXXXXXCYGGGGGSDKTH TCPPCPAPELLGGPSVFLFPPKPKDTLMISRTPEVTC VVVDVSHEDPEVKFNWYVDGVEVHNAKTKPREEQ YNSAYRVVSVLTVLHQDWLNGKEYKCKVSNKALP APIEKTISKAKGQPREPQVYTLPPSRDELTKNQVSLT CLVKGFYPSDIAVEWESNGQPENNYKTTPPVLDSD GSFFLYSKLTVDKSRWQQGNVFSCSVMHEALHNH YTQKSLSLSLEHHHHHH |
| 18 | LFcT322AS7 | MLCGGGSYCXXXXXXXXXXXXCYGGGGGSDKTH TCPPCPAPELLGGPSVFLFPPKPKDTLMISRTPEVTC VVVDVSHEDPEVKFNWYVDGVEVHNAKTKPREEQ YNSAYRVVSVLTVLHQDWLNGKEYKCKVSNKALP APIEKTISKAKGQPREPQVYTLPPSRDELTKNQVSLT CLVKGFYPSDIAVEWESNGQPENNYKTTPPVLDSD GSFFLYSKLTVDKSRWQQGNVFSCSVMHEALHNH YTQKSLSLSLEHHHHHH |
| 19 | MFcG7 | MALMGGGGYCXXXXXXXXXXXXCYGGGGGSDK THTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQVS LTCLVKGFYPSDIAVEWESNGQPENNYKTTPPVLDS DGSFFLYSKLTVDKSRWQQGNVFSCSVMHEALHN HYTQKSLSLSLEHHHHHH |

TABLE 1-continued

Described Sequences

| SEQ ID NO. | Protein | Exemplary Amino Acid Sequence |
|---|---|---|
| 20 | MFcT322AG7 | MALMGGGGYCXXXXXXXXXXXXCYGGGGGSDK THTCPPCPAPELLGGPSVFLFPPKPKDTLMISRTPEV TCVVVDVSHEDPEVKFNWYVDGVEVHNAKTKPRE EQYNSAYRVVSVLTVLHQDWLNGKEYKCKVSNKA LPAPIEKTISKAKGQPREPQVYTLPPSRDELTKNQVS LTCLVKGFYPSDIAVEWESNGQPENNYKTTPPVLDS DGSFFLYSKLTVDKSRWQQGNVFSCSVMHEALHN HYTQKSLSLSLEHHHHHH |
| 21 | Glycine-serine linker | GGGGGS |
| 22 | C$_H$2 domain | LGGPSVFLFPPKPKDTLMISRTPEVTCVVVDVSHED PEVKFNWYVDGVEVHNAKTKPREEQYNSTYRVVS VLTVLHQDWLNGKEYKCKVSNKALPAPIEKTISK |
| 23 | C$_H$3 domain | AKGQPREPQVYTLPPSRDELTKNQVSLTCLVKGFYP SDIAVEWESNGQPENNYKTTPPVLDSDGSFFLYSKL TVDKSRWQQGNVFSCSVMHEALHNHYTQKSLSLS LE |
| 24 | AHNP | FCDGFYACYMDV |
| 25 | AHNPY | YCDGFYACYMDV |
| 26 | AHNP-GG | FCDGFGGCYMDV |
| 27 | WP9QY | YCWSQYLCY |
| 28 | KP7-6 | YCDEHFCY |
| 29 | OP3-4 | YCEIEFCYLIR |
| 30 | reo3Y | FCIYSGSTCY |
| 31 | B2BPT | PCPINCTHSCVDLDDKGCPAEQRASPLTSI |
| 32 | B2APE | YCPIWKFPDEECY |
| 33 | EP1 | YCGYSSTSYCFVMD |
| 34 | EP2 | YCASRDYDYDGRCYFD |
| 35 | EP3 | YCTRGYSSTSYCYAMD |
| 36 | EP4 | FCMEESGGNYCY |
| 37 | EP5 | YCALRGGVYWPCY |
| 38 | EP6 | YCALTYYDYECFAY |
| 39 | CD4CDR3.AME (82-89) | FCYICEVEDQCY |
| 40 | C3 | ICVVQDWGHHRCT |
| 41 | WP5 | YCFTASENHCY |
| 42 | E247-266 | YCPALVTYNTDTFESMPNPEGRCY |
| 43 | CD3 gamma | QSIKGNHLVKVYDYQEDGSVLLTCDAEAKNITWFK DGKMIGFLTEDKKKWNLGSNAKDPRGMYQCKGSQ NKSKPLQVYYRMCQNCIELNAATISGFLFAEIVSIFV LAVGVYFIAGQDGVRQSRASDKQTLLPNDQLYQPL KDREDDQYSHLQGNQLRRN |
| 44 | CD3 epsilon | DGNEEMGGITQTPYKVSISGTTVILTCPQYPGSEILW QHNDKNIGGDEDDKNIGSDEDHLSLKEFSELEQSGY YVCYPRGSKPEDANFYLYLRARVCENCMEMDVMS VATIVIVDICITGGLLLLVYYWSKNRKAKAKPVTRG AGAGGRQRGQNKERPPPVPNPDYEPIRKGQRDLYS GLNQRRI |

The scaffolds and antigen-binding proteins described herein can be made by recombinant processes and, therefore, may include amino acid sequences derived from more than one species (i.e. chimeric constructs) or may be engineered to have a human, or human-like, amino acid composition (i.e., a humanized construct). Accordingly, provided herein are vectors comprising polynucleotides capable of encoding the described scaffolds and antigen-binding proteins. The vectors can be expression vectors. Recombinant expression vectors containing a sequence encoding a polypeptide of interest are thus provided. The expression vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

The vectors described herein can be used to transform various cells with the genes encoding the disclosed scaffolds or antigen-binding proteins. For example, the vectors may be used to generate scaffold or antigen-binding protein-producing cells or cell lines. Thus, another aspect features host cells transformed with vectors comprising a nucleic acid sequence encoding a scaffold or antigen-binding protein, such as the scaffolds or antigen-binding proteins disclosed and exemplified herein. The host cells disclosed herein can be prokaryotic or eukaryotic cells. For example the host cell can be a bacteria. In one embodiment, the bacterial host cell is *E. coli*. Of course, the host cell can also be a mammalian cell, such as a Chinese hamster ovary (CHO) cell line. Numerous other such host cells, prokaryotic and eukaryotic, are known in the art and are considered to be within the scope of this disclosure.

Numerous techniques are known in the art for the introduction of foreign genes into cells and may be used to construct the recombinant cells for purposes of carrying out the inventive methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

Methods of using the described scaffolds, or antigen-binding proteins, are also provided. For example, antigen-binding proteins derived from the scaffolds disclosed herein may be used to treat or prevent disease in a subject. The described methods of treating or preventing disease can be used to administer compositions, having antigen-binding proteins derived from the described scaffolds, to a subject in need of such treatment. In some embodiments, the described methods of treatment can be used to treat a subject having cancer. In some embodiments the methods of treatment described herein can be used to treat a subject having cancer that is susceptible to treatment with a HER2 binding protein, such as a HER2-specific antibody. In some embodiments the methods of treatment described herein can be used to treat a subject having cancer that is susceptible to treatment by preventing HER3 signaling. In some embodiments the methods of treatment described herein can be used to treat a subject having cancer that is susceptible to treatment by disrupting dimerization of HER3. In some embodiments the methods of treatment described herein can be used to treat a subject having cancer that is susceptible to treatment by disrupting dimerization of HER2 and HER3. In some embodiments the methods of treatment described herein can be used to treat a subject having cancer that is known to be resistant to treatment with a HER2-specific antibody. In some embodiments the methods of treatment described herein can be used to treat a subject having cancer that is known to be resistant to treatment with a EGFR-specific antibody. Also disclosed are methods for detecting an antigen of interest using antigen-binding proteins derived from the scaffolds disclosed herein. Such methods are applicable to antigen detection in a subject, in a sample obtained from a subject, or in vitro. The methods described herein can be particularly applicable to treating or preventing diseases associated with HER2 such as administering to a subject an antigen-binding protein capable of interacting with HER2, as disclosed herein, and a pharmaceutically acceptable carrier. Methods described herein can also be used to treat or prevent diseases associated with the EGFR, such as administering to a subject an antigen-binding protein capable of interacting with EGFR, as disclosed herein, and a pharmaceutically acceptable carrier. In addition, methods described herein can also be used to treat or prevent diseases associated with the HER3, such as administering to a subject an antigen-binding protein capable of interacting with HER3, as disclosed herein, and a pharmaceutically acceptable carrier Alternatively, antigen-binding proteins derived from the scaffolds disclosed herein may be used to detect disease-causing agents or disease associated proteins or metabolites in a subject or a sample obtained from a subject, which in turn can allow for a diagnosis. The methods described herein can be particularly applicable to detecting or otherwise assessing the expression of the HER2, EGFR, or HER3 in a subject. For example, one could inject a subject with a detectably labeled embodiment of an antigen-binding protein capable of binding HER2, EGFR, or HER3, as described herein, and detect the localization and/or intensity of the signal in the subject. Alternatively, one could expose a sample containing HER2, EGFR, or HER3 to a described antigen-binding protein and detecting binding of the antigen-binding protein to the sample.

In some embodiments, the disclosed antigen-binding proteins are conjugated to one or more chemotherapeutic agents such as, but not limited to radionuclides, toxins, and cytotoxic and cytostatic agents. In other embodiments the antigen-binding proteins are used in combination with one or more chemotherapeutic agents. The antigen-binding proteins described herein may be used alone or with (e.g., coadministered or conjugated to) a biomolecule or chemotherapeutic agent such as a cytotoxic or cytostatic agent. In some embodiments, the chemotherapeutic agent is a radionuclide, including, but not limited to lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide. In other embodiments, the chemotherapeutic agent is a toxin or cytotoxic drug, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, pemetrexed, cisplatinum, vindesine, adriamycin, vincristine, vinblastine, BCNU, taxol, tarceva, avastin, mitomycin, 5-fluorouracil, cyclophosphamide, certain cytokines such as TNF-alpha and TNF-beta, and the like. Methods of conjugation of scaffolds or antigen-binding proteins to such agents are known in the literature.

Described herein are compositions comprising at least one disclosed scaffold or antigen-binding protein and a pharmaceutically acceptable carrier. The compositions can be formulated as any of various preparations that are known and suitable in the art, including those described and exemplified herein. In some embodiments, the compositions are aqueous formulations. Aqueous solutions can be prepared by admixing the antigen-binding proteins in water or suitable physiologic buffer, and optionally adding suitable colorants, flavors, preservatives, stabilizing and thickening agents and the like as desired. Aqueous suspensions can also be made by dispersing the antigen-binding proteins in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions can be formulated for injection into a subject. For injection, the compositions described can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The antigen-binding proteins described herein may be administered orally in any acceptable dosage form such as capsules, tablets, aqueous suspensions, solutions or the like. The antigen-binding proteins may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the antigen-binding proteins will be intravenously or intraperitoneally, for example, by injection.

The subject can be any animal, and preferably is a mammal such as a mouse, rat, hamster, guinea pig, rabbit, cat, dog, monkey, donkey, cow, horse, pig, and the like. In some instances the subject is a human. In some embodiments, subjects can be administered at least one antigen-binding protein in a daily dose range of about 0.01 µg to about 500 mg of antigen-binding protein per kg of the weight of the subject. The dose administered to the subject can also be measured in terms of total amount of the at least one antigen-binding protein administered per day. In some embodiments, a subject is administered about 5 to about 5000 milligrams of at least one antigen-binding protein per day. In some embodiments, a subject is administered up to about 10 milligrams of at least one a antigen-binding protein per day. In some embodiments, a subject is administered up to about 100 milligrams of at least antigen-binding protein per day. In some embodiments, a subject is administered up to about 250 milligrams of at least one antigen-binding protein per day. In some embodiments, a subject is administered up to about 500 milligrams of at least one antigen-binding protein per day. In some embodiments, a subject is administered up to about 750 milligrams of at least one antigen-binding protein per day. In some embodiments, a subject is administered up to about 1000 milligrams of at least one antigen-binding protein per day. In some embodiments, a subject is administered up to about 1500 milligrams of at least one antigen-binding protein per day. In some embodiments, a subject is administered up to about 2000 milligrams of at least one antigen-binding protein per day. In some embodiments, a subject is administered up to about 2500 milligrams of at least one antigen-binding protein per day. In some embodiments, a subject is administered up to about 3000 milligrams of at least one antigen-binding protein per day. In some embodiments, a subject is administered up to about 3500 milligrams of at least one antigen-binding protein per day. In some embodiments, a subject is administered up to about 4000 milligrams of at least one antigen-binding protein per day. In some embodiments, a subject is administered up to about 4500 milligrams of at least one antigen-binding protein per day. In some embodiments, a subject is administered up to about 5000 milligrams of at least one antigen-binding protein per day. In some embodiments, the antigen-binding protein is administered to a subject weekly or bi-weekly.

For effective treatment, one skilled in the art may recommend a dosage schedule and dosage amount adequate for the subject being treated. It may be preferred that dosing occur one to four or more times daily for as long as needed. The dosing may occur less frequently if the compositions are formulated in sustained delivery vehicles. The dosage schedule may also vary depending on the active drug concentration, which may depend on the needs of the subject.

There are several embodiments that follow from the description provided above, particularly those relating to antigen-binding proteins. In one embodiment, an antigen-binding protein can have at least one protein scaffold and at least one antigen-specific peptide. The antigen-binding proteins described above could be composed from a protein scaffold such as any one, or more, of the protein scaffolds exemplified by the amino acid sequences shown in Table 1. In some embodiments, the protein scaffold will have only the amino acid sequences that are between the glycine-serine linker (GGGGGS) (SEQ ID NO: 21) and the histidine tag (HHHHHH) (SEQ ID NO: 45) of SEQ ID NO:1, SEQ ID NO:2, SEQ ID NO:3, SEQ ID NO:4, SEQ ID NO:5, SEQ ID NO:6, SEQ ID NO:7, SEQ ID NO:16, SEQ ID NO:17, SEQ ID NO:18, SEQ ID NO:19, or SEQ ID NO:20, while in other embodiments the protein scaffold can further include the amino acid segment preceding the antigen-specific peptide for SEQ ID NO:1, SEQ ID NO:2, SEQ ID NO:3, SEQ ID NO:4, SEQ ID NO:5, SEQ ID NO:6, SEQ ID NO:7, SEQ ID NO:16, SEQ ID NO:17, SEQ ID NO:18, SEQ ID NO:19, or SEQ ID NO:20, in addition to other amino acid sequences. In addition, the described antigen-binding proteins can incorporate any number of antigen-specific peptides, such as the antigen-specific peptide of SEQ ID NO:15. Furthermore, the described antigen-binding proteins can incorporate one or more linkers, made of at least one glycine residue, that connect the components of the protein. In a particular embodiment, the linker described above can have an amino acid sequence of, or similar to, that of SEQ ID NO:20. In some embodiments, the linker will have only the amino acid sequence of SEQ ID NO:20, while in other embodiments a linker can include SEQ ID NO:20 in addition to other amino acid sequences. In other embodiments, any of the antigen-binding proteins described herein can have an epitope tag, a fluorophore, a radio isotope, or an enzyme. In a preferred embodiment, the embodied antigen-binding protein has an epitope tag that is a poly-histidine tag.

The described antigen-binding proteins can be encoded by a variety of polynucleotides capable of encoding the amino acid sequences provided herein. These polynucleotides can also be incorporated into vectors useful for the maintenance, replication, and/or expression of the polynucleotides encoding the described antigen-binding proteins or the described portions thereof. The vectors described above can be used to engineer cells to express the antigen-binding proteins or the described portions thereof encoded by the polynucleotides disclosed herein.

Also provided herein are compositions that include at least one of the antigen-binding proteins described herein and a pharmaceutically acceptable carrier. Such compositions are useful in the methods provided herein for treating or preventing disease in a subject. In one embodiment, the described methods of treatment include administering a therapeutic amount of a one or more of the described antigen-binding proteins to a subject in need of such treatment. Similarly, in one embodiment, the described methods of preventing disease in a subject include administering a therapeutic amount of a one or more of the described antigen-binding proteins to a subject in need thereof. A preferred method of treating or preventing a disease relate to a disease associated with HER2, EGFR, or HER3 in a subject, where the treatment or prevention includes administering to the subject a composition including an antigen-binding protein described herein. Also provided are methods of detecting an antigen of interest in a subject that include administering an antigen-binding protein provided herein to a subject and detecting binding of the antigen-binding protein to an antigen of interest. A preferred method of detection involves using at least one of the antigen-binding proteins described to detect HER2 by exposing a sample containing HER2 to an antigen-binding protein capable of binding HER2 and detecting binding of at least one antigen-binding protein to the sample. Another preferred method of detection involves using at least one of the antigen-binding proteins described to detect EGFR by exposing a sample containing EGFR to an antigen-binding protein capable of binding EGFR and detecting binding of at least one antigen-binding protein to the sample. Another preferred method of detection involves using at least one of the antigen-binding proteins described to detect HER3 by exposing a sample containing HER3 to an antigen-binding protein capable of binding HER3 and detecting binding of at least one antigen-binding protein to the sample.

Also provided herein are compositions that include the antigen-binding proteins described herein and a pharmaceutically acceptable carrier. Such compositions are useful in the methods provided herein for treating or preventing disease in a subject. In one embodiment, the described methods of treatment include administering a therapeutic amount of a one or more of the described antigen-binding proteins to a subject in need of such treatment. Similarly, in one embodiment, the described methods of preventing disease in a subject include administering a therapeutic amount of a one or more of the described antigen-binding proteins to a subject in need thereof. A preferred method of treating or preventing a disease relate to a disease, such as cancer, associated with HER2, EGFR, or HER3 in a subject, where the treatment or prevention includes administering to the subject a composition including a antigen-binding protein described herein. Also provided are methods of detecting an antigen of interest in a subject that include administering an antigen-binding protein provided herein to a subject and detecting binding of the antigen-binding protein to an antigen of interest. A preferred method of detection involves using at least one of the antigen-binding proteins described to detect HER2, EGFR, or HER3 by exposing a sample containing one of these receptors to an antigen-binding protein and detecting binding of at least one antigen-binding protein to the sample.

The following examples are provided to further describe some of the embodiments disclosed herein. They are intended to illustrate, not to limit, the disclosed embodiments.

EXAMPLE I

Design and Expression of S22-Fc Constructs

Figure 2:
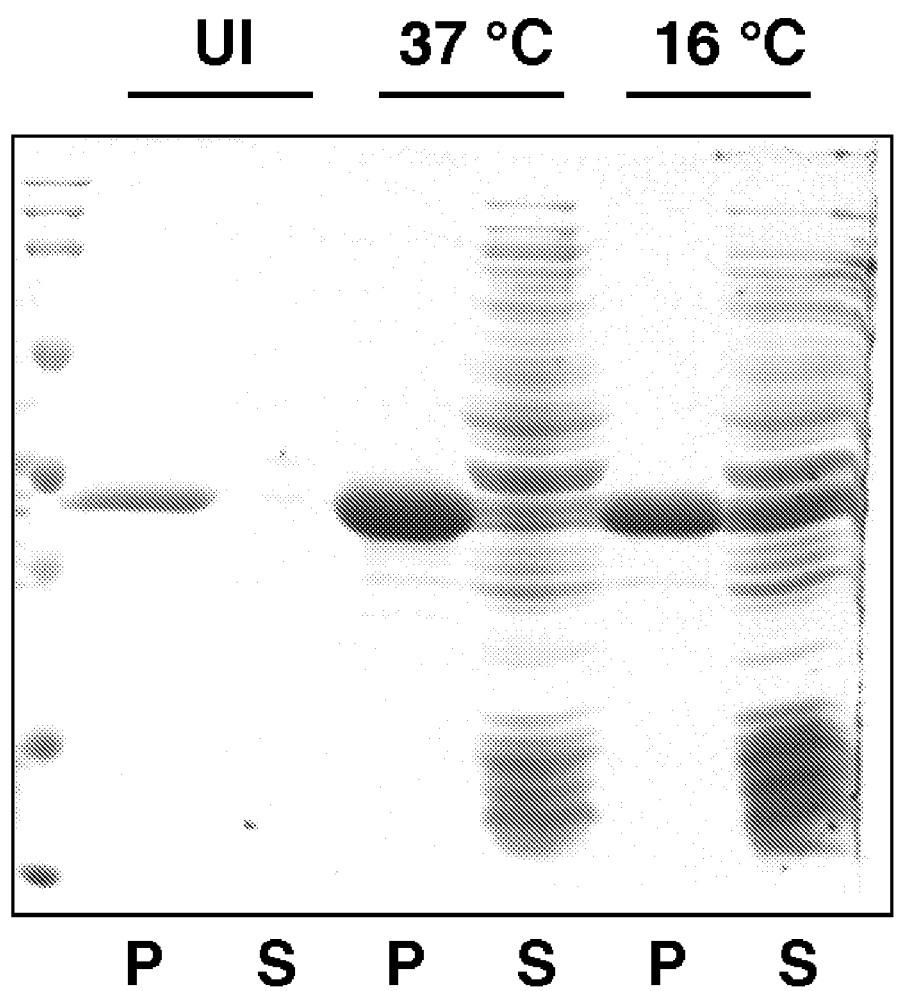
FIG. 2 shows gel-resolved expression of the S22-Fc fusion proteins in BL21(DE3) codon plus (Stratagene, Inc). Expression of recombinant proteins was induced by 0.5 mM IPTG at either 37° C. or 16° C. as indicated. UI: uninduced cells; P: inclusion body of induced cells containing insoluble proteins; S: Soluble proteins from induced cells.

A recombinant expression strategy was developed in order to embed the S22 peptide into an intact Fc antibody segment, having both $C_H2$ and $C_H3$ domains of IgG1 (FIG. 1). Since S22 is a very short peptide, the cDNA for the S22-Fc chimera was produced by PCR using 5' primers containing the S22 sequence. A plasmid containing human IgG1 cDNA clone (ATCC no. 9898675) was used as the PCR template. Proper restriction sites were designed at 5' and 3' ends so the resulting PCR products could be cloned into the E. coli expression vector pET21d (Novagen). E. coli expression was selected because it allows for the rapid production of recombinant proteins. In E. coli, the S22-Fc fusion proteins are predominantly expressed in inclusion bodies as insoluble proteins, but some of it is also present in the soluble fraction, especially when the bacteria are cultured at 16° C. (FIG. 2). Soluble fusion proteins were purified on Ni-sepharose columns according to manufacturer's instructions (GE Healthcare).

FACS analysis was used to detect binding of S22-Fc to HER2-expressing cell lines. Purified S22-Fc was used in FACS experiments to stain cells with different expression levels of HER2 and EGFR. Initially, $1\times10^5$ cells were incubated with 10 μg S22-Fc for 30 minutes on ice. The cells were then washed and incubated with his-tag-specific rabbit antisera and secondary Alexa488-conjugated anti-rabbit antibodies, used sequentially. As a negative control, parallel cell preparations were exposed to only his-tag-specific rabbit antisera and secondary antibodies.

Figure 3:
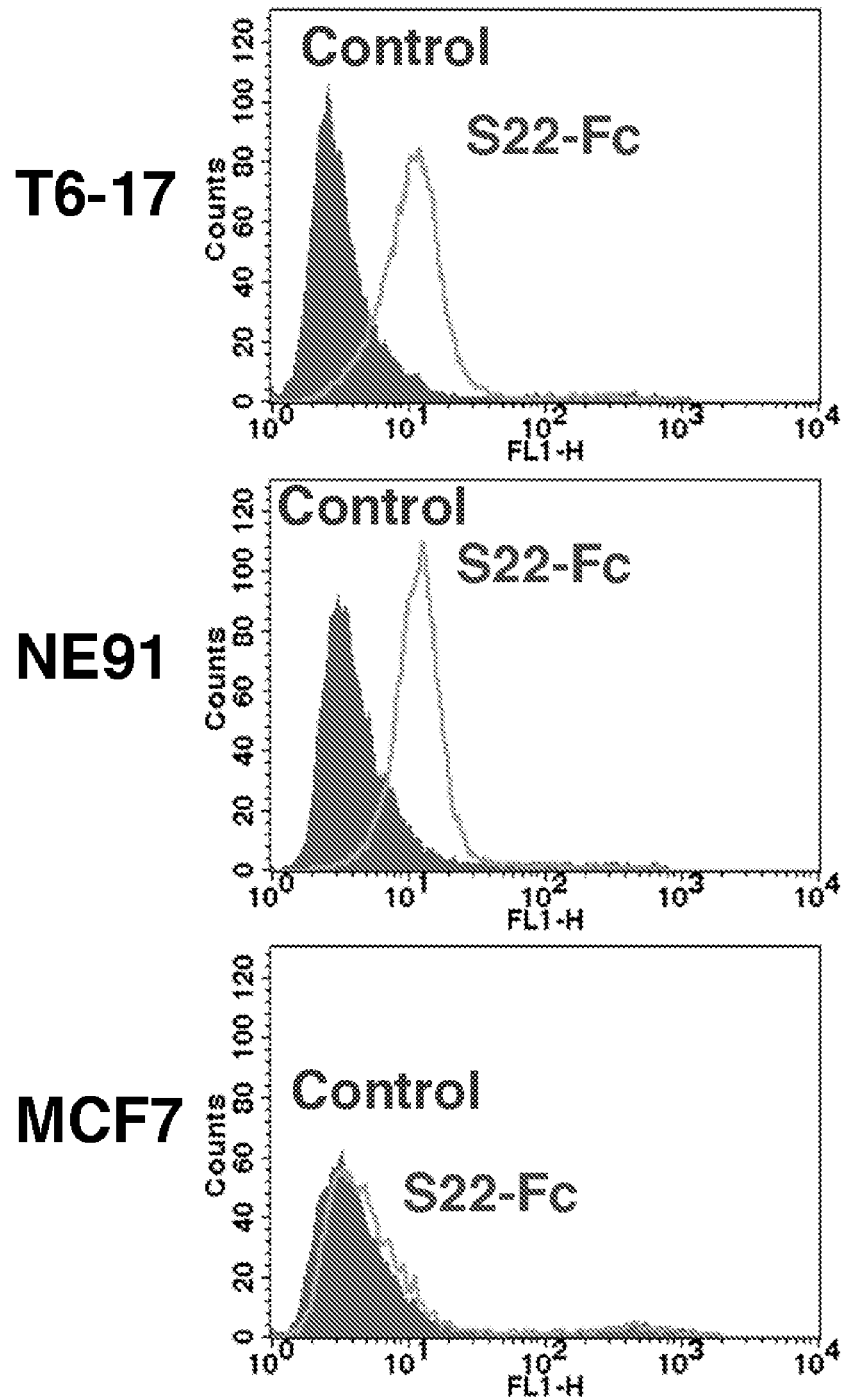
FIG. 3 shows the results of FACS experiments to stain cells (T6-17, NE91, and MCF7) with different expression levels of HER2 and EGFR with purified S22-Fc.

FACS analysis showed that S22-Fc bound to T6-17 cells (a mouse fibroblast engineered to express human HER2) and NE91 cells (A mouse fibroblast cell line engineered to express human EGFR); however, MCF7 cells (a human breast cancer cell line negative for HER2 and minimally positive for EGFR) showed minimal binding (FIG. 3). These data indicate that embedded Fc forms that have S22 CDR binding units and intact Fc regions can be generated and are functional.

EXAMPLE II

Modification of the $C_H2$ Domain of S22-Fc Improves Binding

Figure 4:
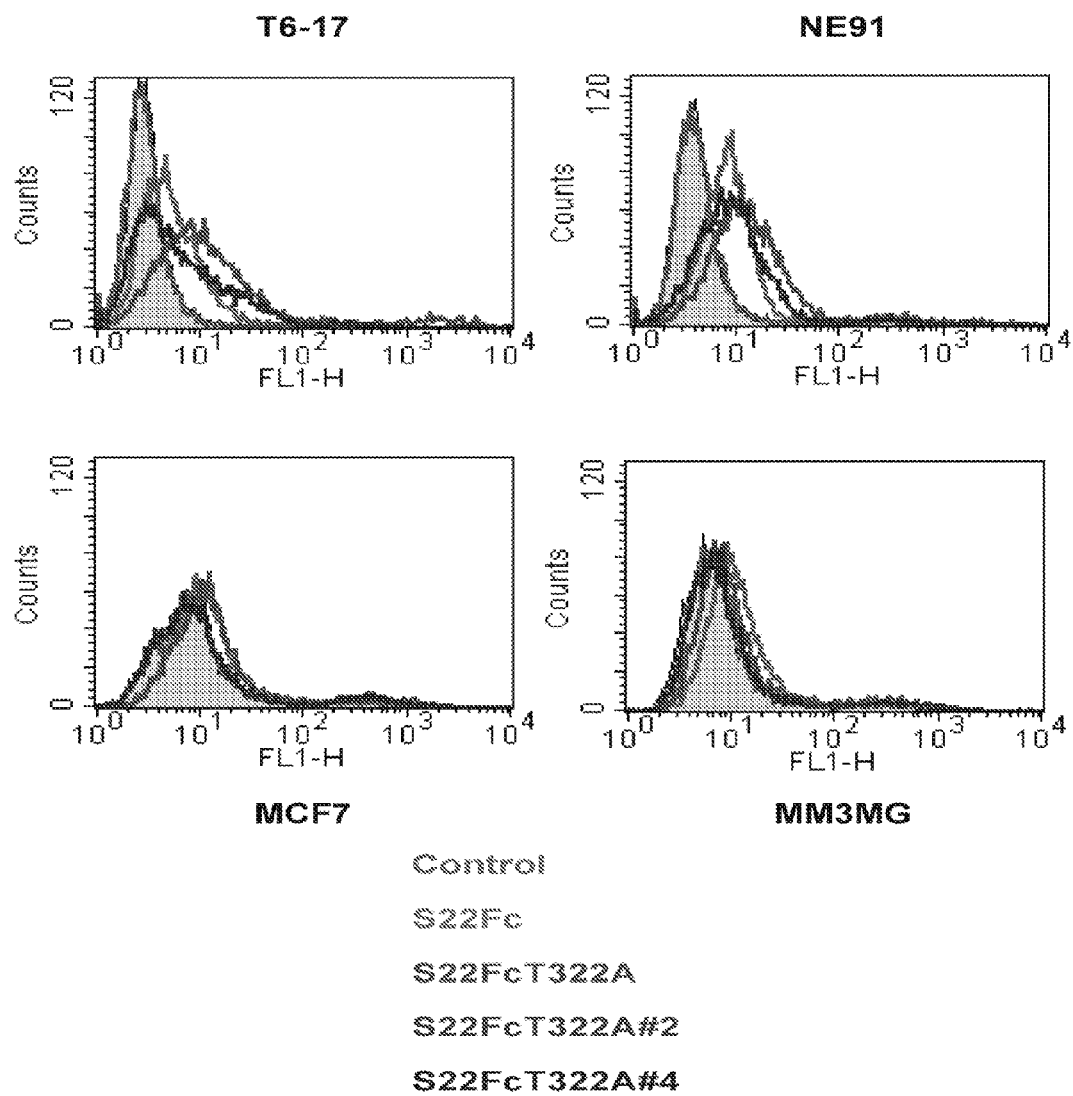
FIG. 4 shows FACS analysis of T6-17, NE91, MCF7, and MM3MG cells stained with antigen-binding proteins S22-Fc, S22-FcT322A, S22-Fc322#2, S22-Fc322#4.

Sazinsky et al. (Proc. Natl. Acad. Sci. U.S.A., 105(51): 20167-72 (2008)), described a T299A mutation near the glycosylation site (N297) in the $C_H2$ domain that dramatically improved the ability of a glycosylated Fc fragment to bind to Fc receptors. This mutation was introduced to the S22-Fc construct in order to improve its binding with Fc receptors. The resulting construct was named S22FcT322A construct (FIG. 4). Unexpectedly, the introduction of this mutation resulted in reduced HER2 (on T6-17 cells) and EGFR (on NE91 cells) binding for S22FcT322A. However, another construct, S22FcT322A#2, which contains the T299A mutation but accidentally expressed several additional amino acids at the N-terminal, possessed better binding than S22-Fc to T6-17 and NE91 cells (FIG. 4). The observed improved binding is expected to be a consequence of improved stability of the construct. No constructs stained the control cell line MM3MG (a murine fibroblast cell line). In addition, the S22-Fc and S22FcT322A#2 constructs also showed some binding to MCF7 cells, which does not overexpress HER2 and EGFR, but is known to express HER3.

Figure 5:
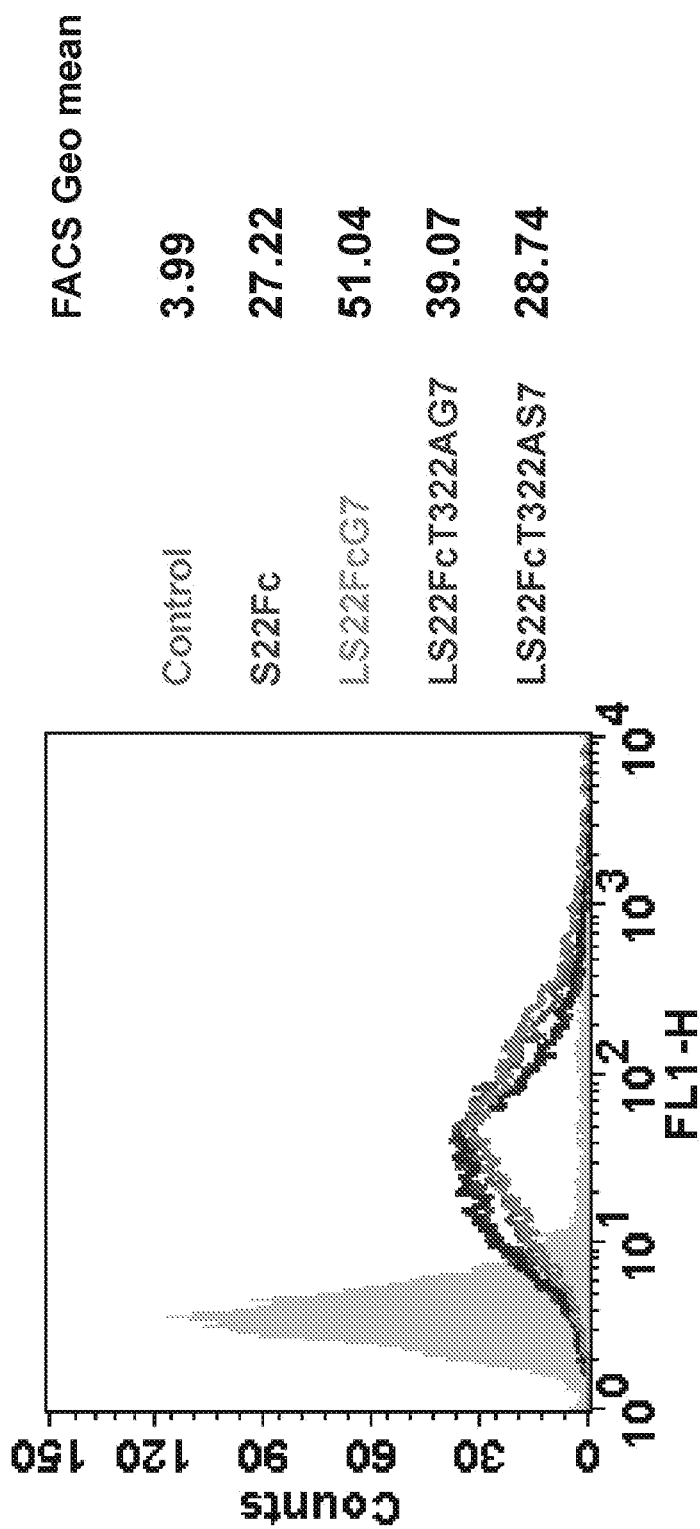
FIG. 5 depicts the results binding of several LS22-Fc constructs to the T6-17 cell line as assessed by FACS analysis. The geometric mean of each construct is also listed. The solid grey peak represents the control cells that were stained only with anti-his tag and secondary antibodies.

Based on these initial findings, additional modifications were made to the S22-Fc construct to produced other derivative fusion proteins: LS22FcG7; LS22FcT322AG7 and LS22FcT322AS7 As shown in FIG. 5, LS22FcG7, which has the wild type Fc fragment, had the highest affinity to T6-17 cells, while LS22FcT322AG7 also bound cells better than S22Fc. Another construct, MS22FcT322AG7, appeared to exhibit even greater binding as observed by FACS analysis (data not shown).

EXAMPLE III

Inhibition of Tumor Growth

Figure 6:
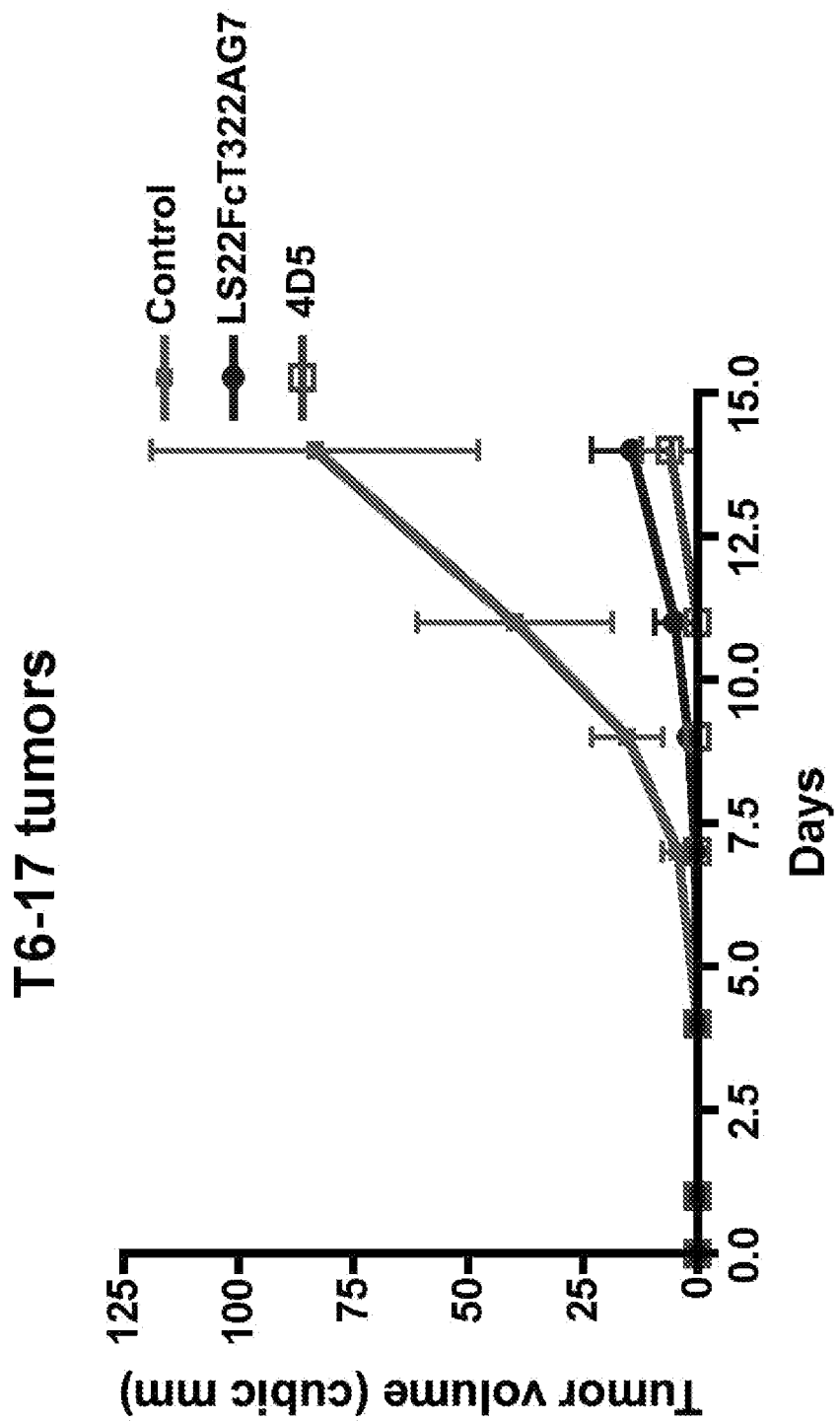
FIG. 6 shows inhibition of tumor growth in athymic mice carrying HER2-positive T6-17 xenografts treated with either LS22FcT322AG7, the 4D5 antibody, or buffer.

The LS22FcT322AG7 antigen-binding protein was tested to assess its ability to inhibit tumor growth in vivo. In these experiments LS22FcT322AG7 was tested against the anti-HER2 antibody 4D5 (positive control) for the ability to inhibit tumors induced by the T6-17 cell line that expresses human HER2/neu. Initially, $5\times10^4$ T6-17 cells were subcutaneously inoculated into athymic nude mice. Mice carrying a tumor received either LS22FcT322AG7, the 4D5 antibody, or control buffer at the dose of 10 mg/kg, three times per week via intraperitoneal (i.p.) injection. As shown in FIG. 6, both LS22FcT322AG7 and the 4D5 antibody inhibited tumor growth.

Figure 7:
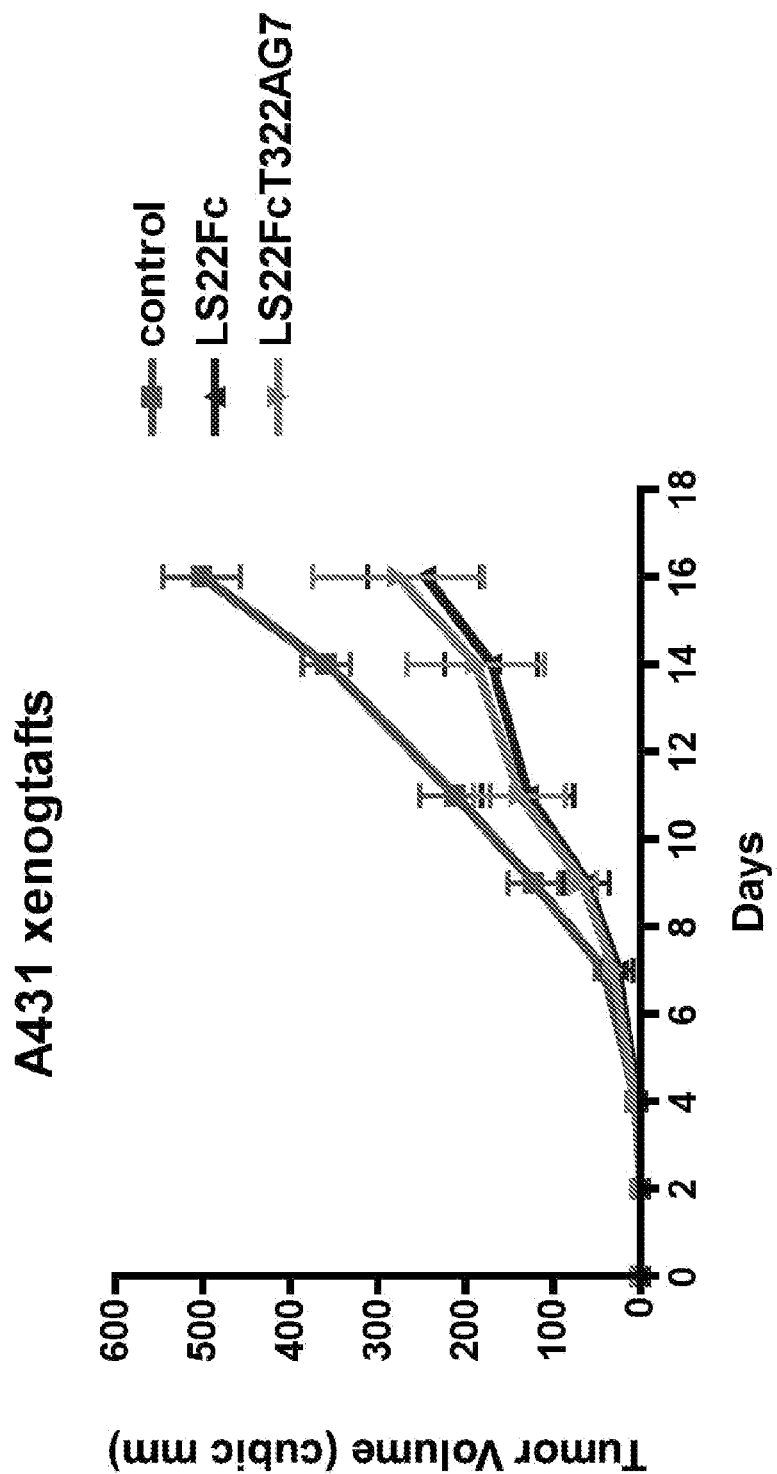
FIG. 7 shows inhibition of tumor growth in athymic mice carrying EGFR-positive A431 xenografts treated with either LS22Fc, LS22FcT322AG7, or buffer.
Figure 8A:
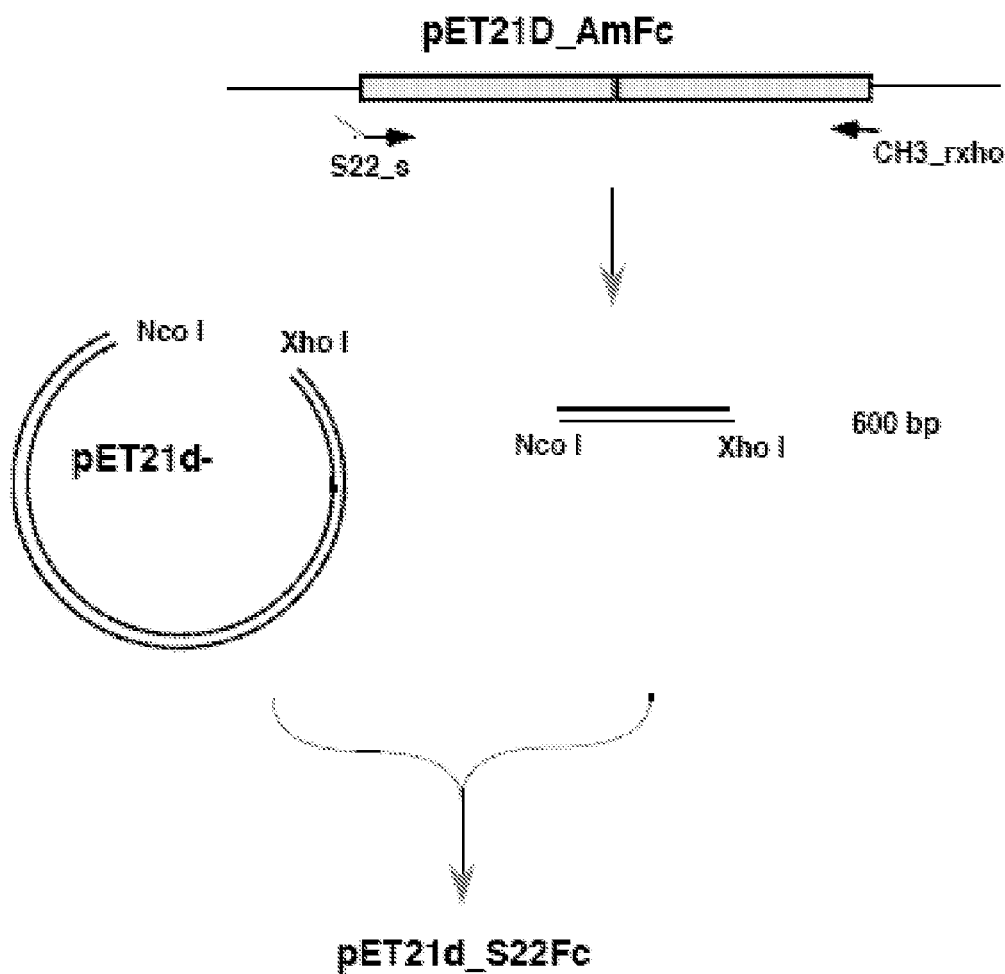
FIGS. 8a-8d provide illustrations of the vector design strategy for the antigen-binding protein constructs S22-Fc (8a), S22-FcT322A#4 (8b), LS22-Fc (8c), LS22-FcT322A (8d).
Figure 8B:
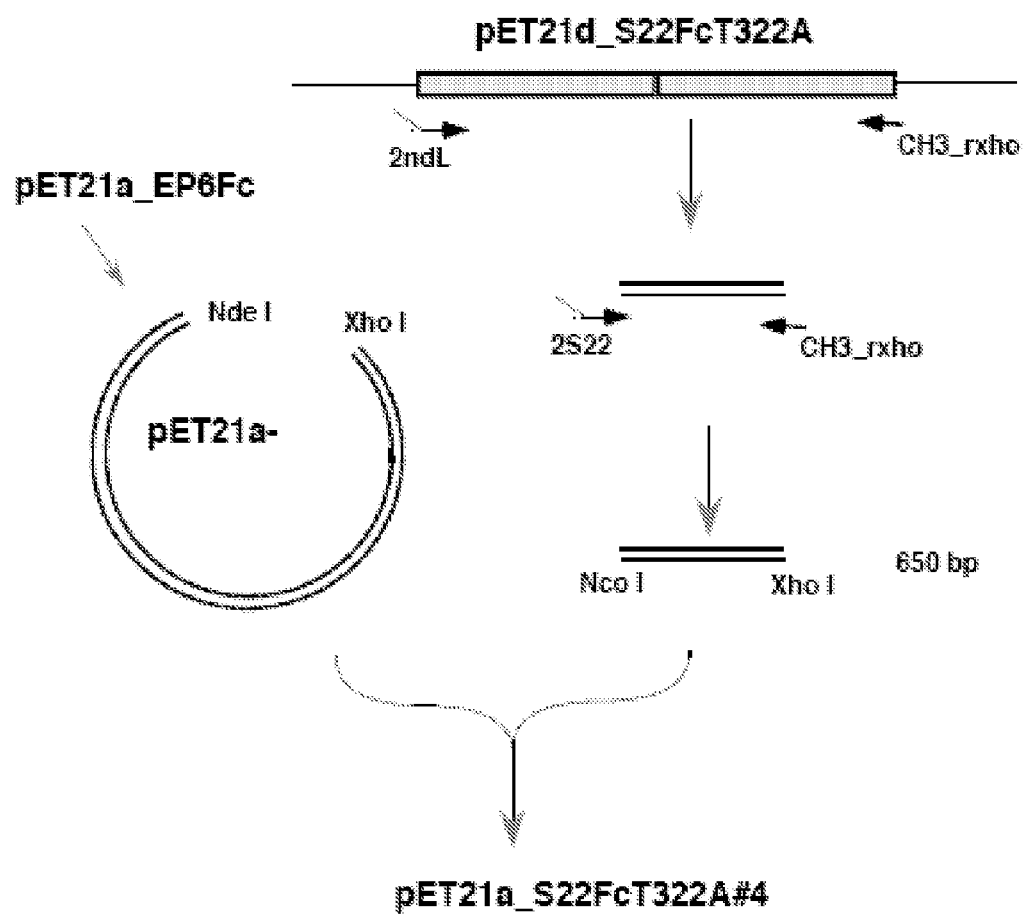
Figure 8C:
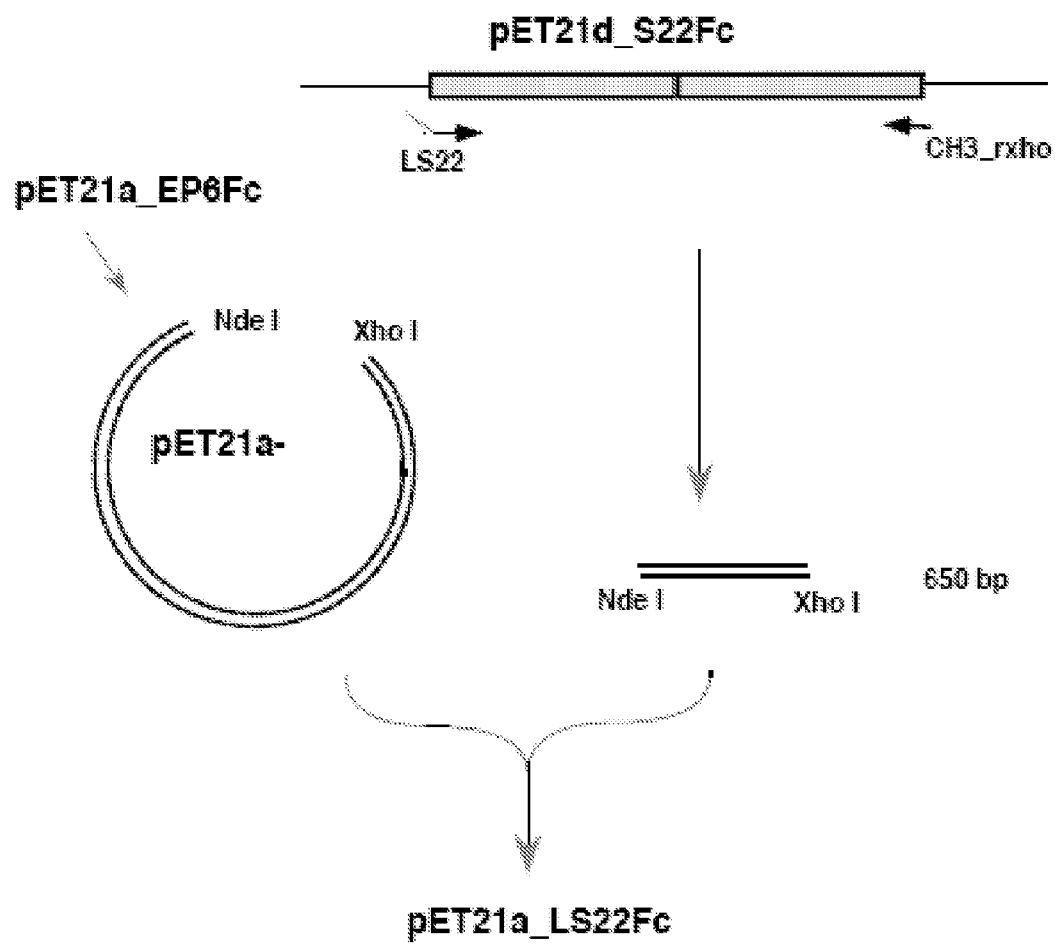
Figure 8D:
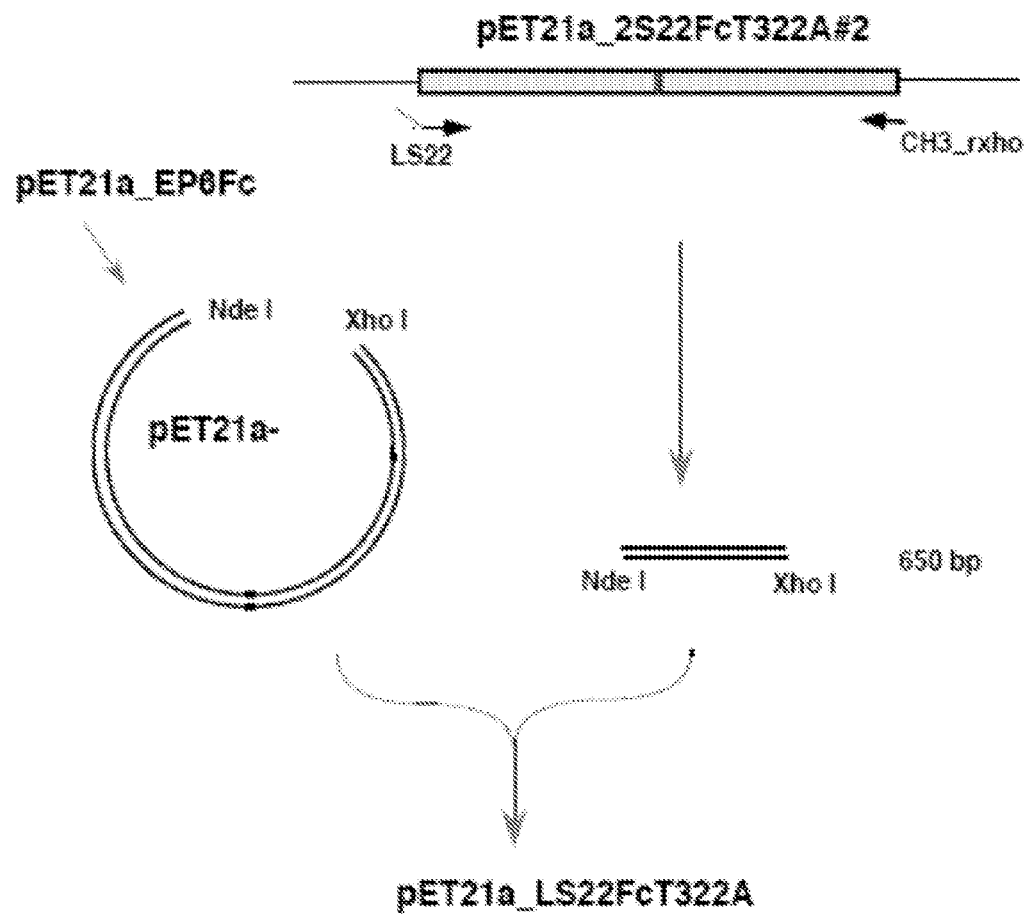

Since S22-Fc antigen-binding proteins also bind to EGFR, experiments were conducted to determine if some of these constructs could also inhibit tumor xenografts induced by the A431 cell line, which overexpresses human EGFR. For these experiments, $1\times10^6$ A431 cells were subcutaneously inoculated into athymic nude mice. Mice carrying tumor received LS22FcT322AG7, LS22Fc or control buffer at the dose of 10 mg/kg, three times per week via i.p. injection. As shown in FIG. 7, both LS22FcT322AG7 and LS22Fc demonstrated activity in the inhibition of A431 tumor growth.

EXAMPLE IV

LS22FcT322AG7 Blocks Binding of HER2-Specific Antibodies

Figure 9:
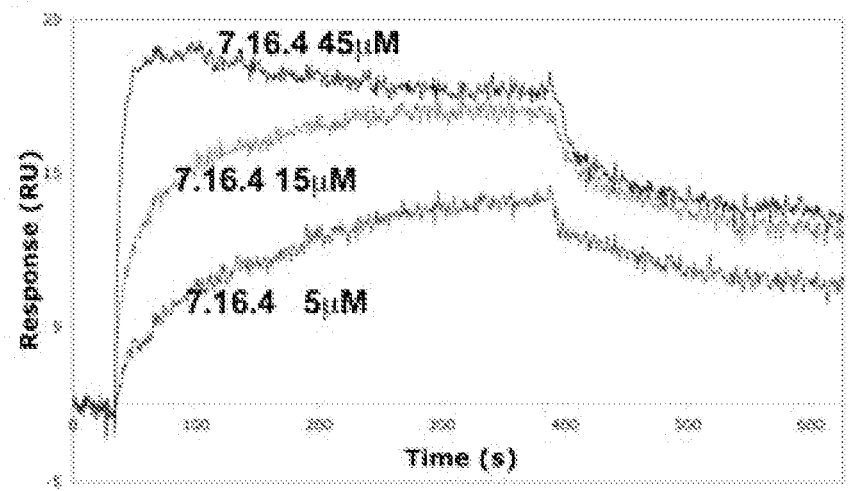
FIG. 9 shows binding of the HER2-specific antibody 7.16.4 to LS22FcT322AG7 (A) and that interaction of the murine HER2-specific antibody 4D5 with HER2 is inhibited in the presence of LS22FcT322AG7 (B). In subpart (B), excluding the left-most control peak, the right-most peak represents binding of m4D5 alone, the center peak represents binding of m4D5 in the presence of LS22FcT322AG7 (10 µg), and the left peak represents binding of m4D5 in the presence of LS22FcT322AG7 (50 µg).
Figure 9:
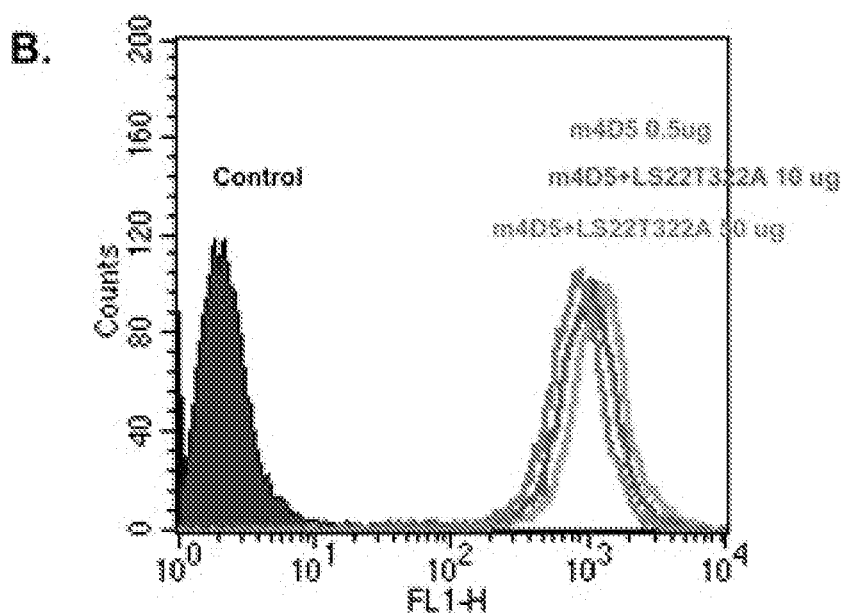

The antigen-binding protein LS22FcT322AG7 contains the S22 loop from HER2, which is located within subdomain IV of the receptor's extracellular domain, where the anti-HER2 antibody 4D5 (trastuzumab) binds (Cho et al., Nature 421:756-760 (2003)). Given these characteristics, experiments were conducted to determine whether antigen-binding protein LS22FcT322AG7 could bind to antibodies that are specific for HER2 and also whether antigen-binding protein LS22FcT322AG7 could block binding of antibodies specific for HER2. For these studies, Biacore experiments were carried out using purified LS22FcT322A immobilized to sensor chip following the standard amine coupling procedure according to the manufacturer's instructions. Then variable concentrations (5 μM, 15 μM, 45 μM) of HER2-specific antibody 7.16.4 (Drebin, J. A., et al., Nature 312:545-548 (1984)) were run over the chip surface to determine binding affinity. As shown in FIG. 9A, binding kinetics were observed for each concentration of antibody 7.16.4. The binding affinity of antibody 7.16.4 for LS22FcT322AG7 was determined to be a $K_D$ of 1.4 μM. FACS experiments were then carried out to determine whether the antigen-binding protein LS22FcT322AG7 could inhibit binding of the murine 4D5 antibody (m4D5) to HER2/neu receptors on T6-17 cells in a dose-dependent manner. For these experiments human HER2-expressing T6-17 cells were incubated with antibody m4D5 in the presence of different concentrations (0 μg, 10 μg, or 50 μg) of LS22FcT322AG7. FITC-labeled anti-mouse secondary antibody was used to detect m4D5 bound to cells. As shown in FIG. 9B, reduced binding of m4D5 was observed in the presence of LS22FcT322AG7 and occurred in a dose-dependent manner. These data indicate that LS22FcT322AG7 could be used to target, and disrupt, HER2 interactions that occur through domain IV of the receptor.

EXAMPLE V

Figure 10:
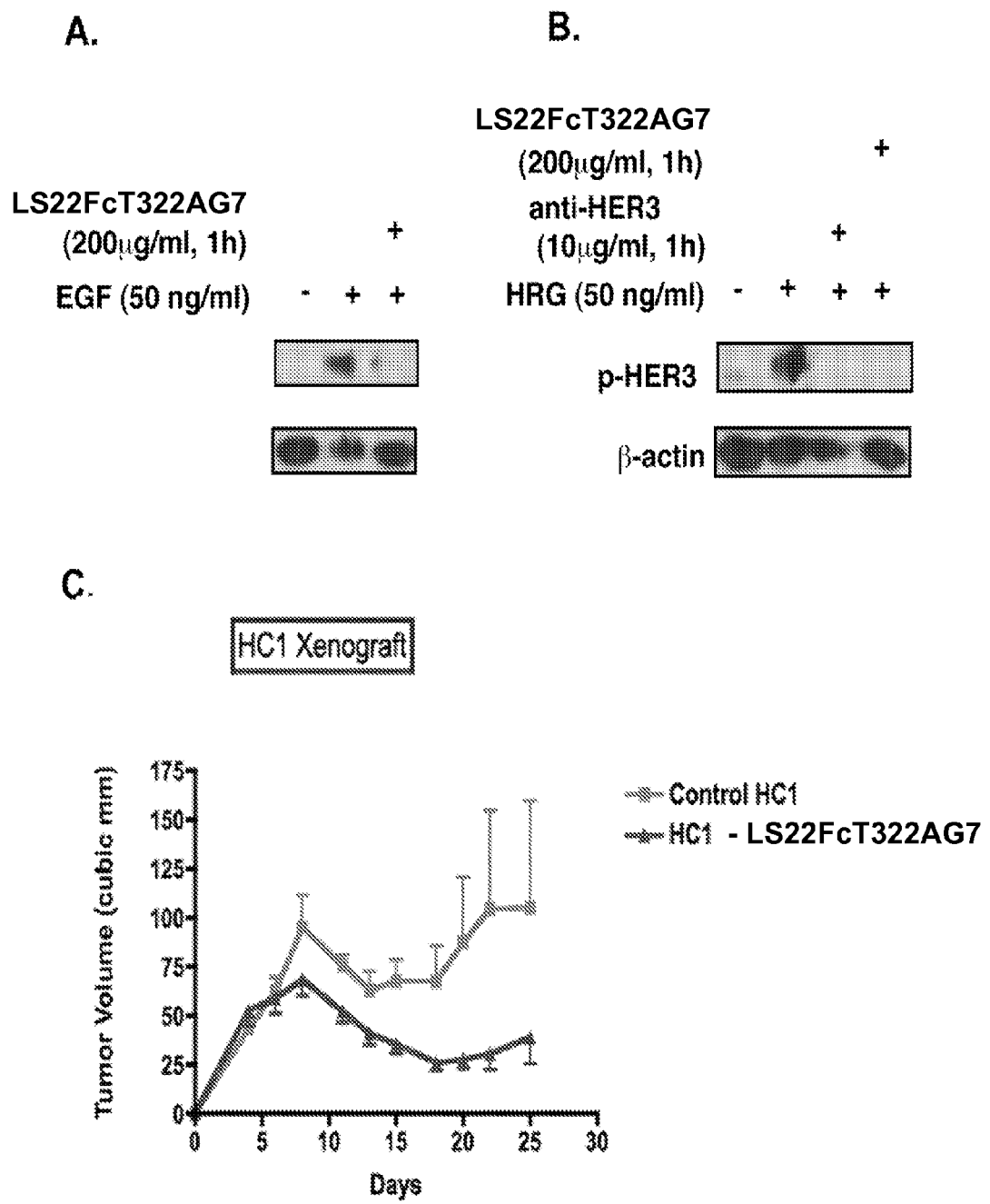
FIG. 10 depicts a Western blot that show reduced EGF-induced phosphorylation of HER3 in the presence of LS22FcT322AG7 (A), a Western blot that show reduced HRG-induced phosphorylation of HER3 in the presence of LS22FcT322AG7 or an anti-HER3 antibody (positive control) (B), reduced in vivo HCl tumor growth in the presence of LS22FcT322AG7, and (C) HCl xenographs implanted subcutaneously into athymic mice.

LS22FcT322AG7 is Effective Against Tumor Cells that Resist Treatment with Anti-EGFR and Anti-HER2 Antibodies The tumor cell line HCl has been previously characterized as being resistant to treatment with cetuximab, an EGFR-specific antibody that is FDA-approved for treating cancer (Wheeler et al., Oncogene 27(28):3944-56 (2008)). The cell line has also been shown to have increased levels of heterodimeric ErbB receptors (Id.). Experiments were conducted to assess whether HCl cells were sensitive to treatment with LS22FcT322AG7. Initial experiments showed that the presence of LS22FcT322AG7 could prevent epidermal growth factor (EGF) and heregulin (HGR)-mediated HER3 activation in cultured HCl cells (FIGS. 10A and 10B). Furthermore, treatment with 10 mg/kg per week of LS22FcT322AG7 was shown to reduce the growth of HCl xenografts implanted subcutaneously into athymic mice (FIG. 10C).

Figure 11:
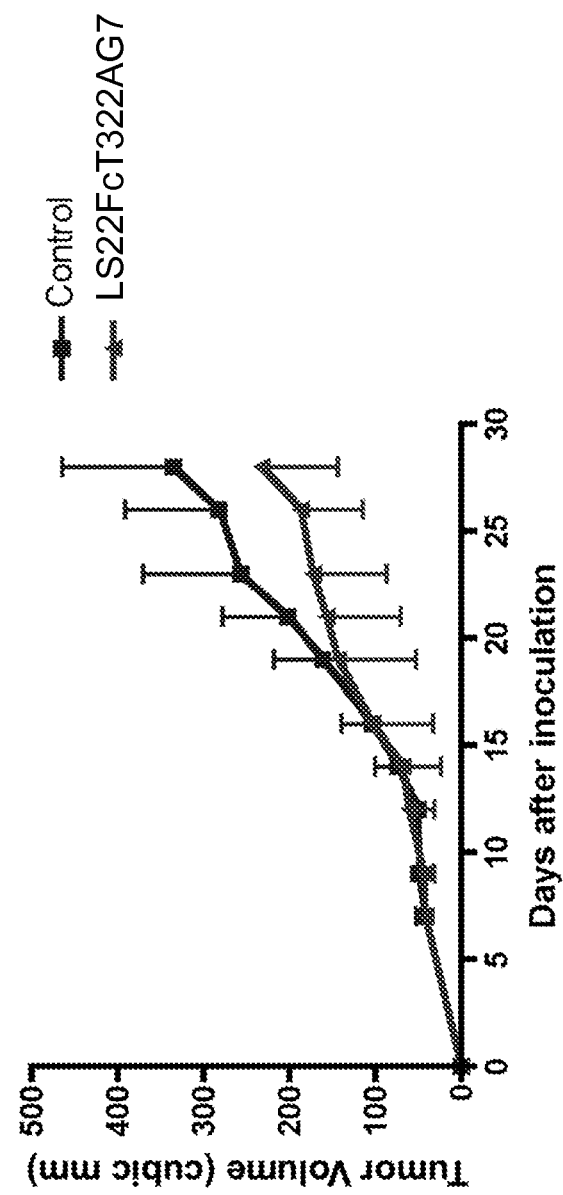
FIG. 11 shows and reduced in vivo TB129 tumor growth in the presence of LS22FcT322AG7.

Further studies were conducted to assess the ability of LS22FcT322AG7 to inhibit the growth of xenographs in mice from the human breast cancer cell line TB129, which was derived from patients who did not respond to treatment with trastuzumab (anti-HER2 antibody). These cells express HER2, but are resistant to trastuzumab in vitro and in vivo. For these experiments tumor cell line TB129 was implanted into nude mice subcutaneously. Nine days after implantation, mice started to receive intraperitoneal treatment with 10 mg/kg of LS22FcT322AG7 three times per week. As shown in FIG. 11, tumor growth was inhibited in mice treated with LS22FcT322AG7 versus mice receiving no treatment (control)).

What is claimed:

1. A recombinant antigen-binding protein comprising the amino acid sequence of SEQ ID NO:1, 2, 3, 4, 5, 6, or 7.

2. A recombinant antigen-binding protein comprising the protein scaffold of SEQ ID NO:14, 16, 17, 18, 19, or 20.

3. The recombinant antigen-binding protein of claim 2, further comprising an antigen-specific peptide of SEQ ID NO:15, 24, 25, 26, 27, 28, 29, 30, 31, 32, 33, 34, 35, 36, 37, 38, 39, 40, 41, 42, 43, or 44.

4. The recombinant antigen-binding protein of claim 2, further comprising an epitope tag, a fluorophore, a radio isotope, or an enzyme.

5. The recombinant antigen-binding protein of claim 4, wherein said epitope tag is a poly-histidine tag.

6. A composition comprising the recombinant antigen-binding protein of claim 1 and a pharmaceutically acceptable carrier.

7. A composition comprising the recombinant antigen-binding protein of claim 2 and a pharmaceutically acceptable carrier.

* * * * *